United States Patent
Nautiyal et al.

(10) Patent No.: US 10,822,642 B2
(45) Date of Patent: Nov. 3, 2020

(54) METHODS OF ANALYSIS OF METHYLATION

(71) Applicant: AFFYMETRIX, INC., Carlsbad, CA (US)

(72) Inventors: Shivani Nautiyal, Portola Valley, CA (US); Malek Faham, Pacifica, CA (US)

(73) Assignee: Affymetrix, Inc., Carlsbad, CA (US)

( * ) Notice: Subject to any disclaimer, the term of this patent is extended or adjusted under 35 U.S.C. 154(b) by 0 days.

(21) Appl. No.: 16/528,222

(22) Filed: Jul. 31, 2019

(65) Prior Publication Data

US 2020/0024640 A1 Jan. 23, 2020

Related U.S. Application Data

(60) Division of application No. 15/281,721, filed on Sep. 30, 2016, now Pat. No. 10,407,717, which is a division of application No. 11/923,649, filed on Oct. 24, 2007, now abandoned, which is a continuation-in-part of application No. 11/739,654, filed on Apr. 24, 2007, now Pat. No. 7,754,451, which is a continuation of application No. 10/300,311, filed on Nov. 19, 2002, now Pat. No. 7,208,295.

(60) Provisional application No. 60/331,693, filed on Nov. 19, 2001, provisional application No. 60/862,735, filed on Oct. 24, 2006.

(51) Int. Cl.
| | | |
|---|---|---|
| *C12Q 1/683* | (2018.01) | |
| *C12Q 1/6813* | (2018.01) | |
| *C12Q 1/6806* | (2018.01) | |

(52) U.S. Cl.
CPC ........... *C12Q 1/683* (2013.01); *C12Q 1/6806* (2013.01); *C12Q 1/6813* (2013.01); *C12Q 2521/331* (2013.01); *C12Q 2523/125* (2013.01); *C12Q 2600/154* (2013.01)

(58) Field of Classification Search
CPC .... C12Q 1/683; C12Q 1/6813; C12Q 1/6806; C12Q 2600/154; C12Q 2521/331; C12Q 2523/125
See application file for complete search history.

(56) References Cited

U.S. PATENT DOCUMENTS

| | | | |
|---|---|---|---|
| 4,945,051 A | 7/1990 | Kikuchi et al. | |
| 5,118,604 A | 6/1992 | Weissman et al. | |
| 5,185,243 A | 2/1993 | Ullman et al. | |
| 5,217,889 A | 6/1993 | Roninson et al. | |
| 5,439,793 A | 8/1995 | Rose et al. | |
| 5,491,063 A | 2/1996 | Fisher et al. | |
| 5,508,178 A | 4/1996 | Rose et al. | |
| 5,525,494 A | 6/1996 | Newton | |
| 5,565,340 A | 10/1996 | Chenchik et al. | |
| 5,580,730 A | 12/1996 | Okamoto | |
| 5,582,989 A | 12/1996 | Caskey et al. | |
| 5,595,891 A | 1/1997 | Rose et al. | |
| 5,612,199 A | 3/1997 | Western et al. | |
| 5,710,000 A | 1/1998 | Sapolsky et al. | |
| 5,728,526 A | 3/1998 | George, Jr. et al. | |
| 5,731,171 A | 3/1998 | Bohlander | |
| 5,786,146 A | 7/1998 | Herman et al. | |
| 5,851,770 A | 12/1998 | Babon et al. | |
| 5,871,917 A | 2/1999 | Duffy | |
| 5,882,856 A | 3/1999 | Shuber | |
| 5,888,731 A | 3/1999 | Yager et al. | |
| 5,912,147 A | 6/1999 | Stoler et al. | |
| 5,928,905 A | 7/1999 | Stemmer et al. | |
| 5,942,609 A | 8/1999 | Hunkapiller et al. | |
| 5,952,176 A | 9/1999 | McCarthy et al. | |
| 6,017,704 A | 1/2000 | Herman et al. | |
| 6,045,994 A | 4/2000 | Zabeau et al. | |
| 6,117,679 A | 9/2000 | Stemmer | |
| 6,130,073 A | 10/2000 | Eggerding | |
| 6,150,516 A | 11/2000 | Brenner et al. | |
| 6,156,501 A | 12/2000 | McGall et al. | |
| 6,200,756 B1 | 3/2001 | Herman et al. | |

(Continued)

FOREIGN PATENT DOCUMENTS

| | | |
|---|---|---|
| EP | 0799897 A1 | 10/1997 |
| EP | 0971039 A2 | 1/2000 |

(Continued)

OTHER PUBLICATIONS

Adorjan et al., Tumor class prediction and discovery by microarray-based DNA methylation analysis, Nucleic Avids Research, 2002, vol. 30, No. 5, e21, Oxford University Press.

(Continued)

*Primary Examiner* — Angela M. Bertagna
(74) *Attorney, Agent, or Firm* — Affymetrix, Inc.; Jinhee Chang

(57) ABSTRACT

Methods for determining the methylation status of a plurality of cytosines are disclosed. In some aspects genomic DNA target sequences containing CpGs are targeted for analysis by multiplex amplification using target specific probes that can be specifically degraded prior to amplification. The targets may be modified with bisulfite prior to amplification. In another aspect targets are cut with methylation sensitive or insensitive restriction enzymes and marked with a tag using the target specific probes. The presence or absence of methylation may be determined using methylation sensitive restriction enzyme or bisulfite treatment. Detection in many embodiments employs hybridization to tag arrays, genotyping arrays or resequencing arrays.

6 Claims, 17 Drawing Sheets
Specification includes a Sequence Listing.

(56) References Cited

U.S. PATENT DOCUMENTS

| | | |
|---|---|---|
| 6,207,372 B1 | 3/2001 | Shuber |
| 6,207,424 B1 | 3/2001 | Chou et al. |
| 6,214,556 B1 | 4/2001 | Olek et al. |
| 6,251,594 B1 | 6/2001 | Gonzalgo et al. |
| 6,300,071 B1 | 10/2001 | Vuylsteke et al. |
| 6,309,823 B1 | 10/2001 | Cronin et al. |
| 6,326,145 B1 | 12/2001 | Whitcombe et al. |
| 6,331,393 B1 | 12/2001 | Laird et al. |
| 6,350,580 B1 | 2/2002 | Sorge |
| 6,355,422 B1 | 3/2002 | Liu et al. |
| 6,361,942 B1 | 3/2002 | Coull et al. |
| 6,383,754 B1 | 5/2002 | Kaufman et al. |
| 6,410,278 B1 | 6/2002 | Notomi et al. |
| 6,509,160 B1 | 1/2003 | Sapolsky et al. |
| 6,514,698 B1 | 2/2003 | Lopez et al. |
| 6,562,569 B1 | 5/2003 | Dale |
| 6,562,659 B1 | 5/2003 | Izumi et al. |
| 6,605,432 B1 | 8/2003 | Huang |
| 6,613,511 B1 | 9/2003 | Schmidt et al. |
| 6,649,347 B2 | 11/2003 | Luo et al. |
| 6,677,121 B2 | 1/2004 | Lizardi et al. |
| 6,713,258 B2 | 3/2004 | Kilian |
| 6,884,586 B2 | 4/2005 | Van et al. |
| 7,208,295 B2 | 4/2007 | Faham et al. |
| 7,754,451 B2 | 7/2010 | Faham et al. |
| 10,407,717 B2 * | 9/2019 | Nautiyal ............ C12Q 1/683 |
| 2001/0046669 A1 | 11/2001 | McCobmie et al. |
| 2001/0049125 A1 | 12/2001 | Stemmer et al. |
| 2002/0006623 A1 | 1/2002 | Bradley et al. |
| 2002/0086324 A1 | 7/2002 | Laird et al. |
| 2002/0102591 A1 | 8/2002 | Sorge |
| 2002/0119448 A1 | 8/2002 | Sorge et al. |
| 2002/0123053 A1 | 9/2002 | Luo et al. |
| 2002/0137036 A1 | 9/2002 | Sorge et al. |
| 2002/0137086 A1 | 9/2002 | Olek et al. |
| 2002/0197639 A1 | 12/2002 | Shia et al. |
| 2003/0022215 A1 | 1/2003 | Makrigiorgos |
| 2003/0032026 A1 | 2/2003 | Berlin |
| 2003/0036081 A1 | 2/2003 | Adorjan et al. |
| 2003/0068620 A1 | 4/2003 | Markowitz et al. |
| 2003/0082600 A1 | 5/2003 | Olek et al. |
| 2003/0082609 A1 | 5/2003 | Olek et al. |
| 2003/0096289 A1 | 5/2003 | Suzuki et al. |
| 2003/0096291 A1 | 5/2003 | Faham et al. |
| 2003/0099997 A1 | 5/2003 | Bestor |
| 2003/0104459 A1 | 6/2003 | Faham et al. |
| 2003/0104464 A1 | 6/2003 | Berlin et al. |
| 2003/0113737 A1 | 6/2003 | Pedersen |
| 2003/0119025 A1 | 6/2003 | Olek et al. |
| 2003/0129602 A1 | 7/2003 | Huang |
| 2003/0129620 A1 | 7/2003 | Olek et al. |
| 2003/0143606 A1 | 7/2003 | Olek et al. |
| 2003/0148290 A1 | 8/2003 | Cottrell |
| 2003/0148326 A1 | 8/2003 | Olek et al. |
| 2003/0148327 A1 | 8/2003 | Olek et al. |
| 2003/0162194 A1 | 8/2003 | Olek et al. |
| 2003/0170684 A1 | 9/2003 | Fan |
| 2003/0170689 A1 | 9/2003 | Stamatoyannapoulos et al. |
| 2003/0180779 A1 | 9/2003 | Lofton-Day et al. |
| 2003/0212455 A1 | 11/2003 | Van et al. |
| 2003/0215842 A1 | 11/2003 | Sledziewski et al. |
| 2003/0224040 A1 | 12/2003 | Baylin et al. |
| 2004/0023230 A1 | 2/2004 | Olek et al. |
| 2004/0023282 A1 | 2/2004 | Luo et al. |
| 2004/0029128 A1 | 2/2004 | Cottrell et al. |
| 2004/0038254 A1 | 2/2004 | Peoples et al. |
| 2004/0048275 A1 | 3/2004 | Guldberg |
| 2004/0072197 A1 | 4/2004 | Jones et al. |
| 2004/0081976 A1 | 4/2004 | Sidransky et al. |
| 2004/0086944 A1 | 5/2004 | Grigg et al. |
| 2004/0115663 A1 | 6/2004 | Berlin et al. |
| 2004/0146868 A1 | 7/2004 | Cottrell et al. |
| 2004/0152080 A1 | 8/2004 | Berlin |
| 2004/0224352 A1 | 11/2004 | Fan et al. |
| 2004/0248090 A1 | 12/2004 | Olek et al. |
| 2005/0009059 A1 | 1/2005 | Shapero et al. |
| 2005/0021240 A1 | 1/2005 | Berlin et al. |
| 2005/0064428 A1 | 3/2005 | Berlin |
| 2005/0196792 A1 | 9/2005 | Fodor et al. |
| 2005/0227265 A1 | 10/2005 | Barany et al. |
| 2005/0266417 A1 | 12/2005 | Barany et al. |
| 2006/0292585 A1 | 12/2006 | Nautiyal et al. |

FOREIGN PATENT DOCUMENTS

| | | |
|---|---|---|
| EP | 1020534 A1 | 7/2000 |
| EP | 1312685 A2 | 5/2003 |
| EP | 1344832 A1 | 9/2003 |
| WO | WO-9633207 A1 | 10/1996 |
| WO | WO-9641012 A1 | 12/1996 |
| WO | WO-9745559 A1 | 12/1997 |
| WO | WO-9949293 A2 | 9/1999 |
| WO | WO-9966071 A1 | 12/1999 |
| WO | WO-0106012 A1 | 1/2001 |
| WO | WO-0132922 A2 | 5/2001 |
| WO | WO-0138556 A1 | 5/2001 |
| WO | WO-0138565 A2 | 5/2001 |
| WO | WO-0177377 A2 | 10/2001 |
| WO | WO-0194625 A2 | 12/2001 |
| WO | WO-0200927 A2 | 1/2002 |
| WO | WO-0204686 A2 | 1/2002 |
| WO | WO-0218649 A1 | 3/2002 |
| WO | WO-0229112 A1 | 4/2002 |
| WO | WO-0234942 A2 | 5/2002 |
| WO | WO-0236821 A2 | 5/2002 |
| WO | WO-02059354 A2 | 8/2002 |
| WO | WO-02059355 A2 | 8/2002 |
| WO | WO-02070751 A1 | 9/2002 |
| WO | WO-02083705 A1 | 10/2002 |
| WO | WO-03023065 A1 | 3/2003 |
| WO | WO-03025215 A1 | 3/2003 |
| WO | WO-03027259 A2 | 4/2003 |
| WO | WO-03048732 A2 | 6/2003 |
| WO | WO-03064682 A1 | 8/2003 |
| WO | WO-03076666 A1 | 9/2003 |
| WO | WO-2004048555 A1 | 6/2004 |
| WO | WO-2004096825 A1 | 11/2004 |
| WO | WO-2005021778 A2 | 3/2005 |
| WO | WO-2005021802 A2 | 3/2005 |

OTHER PUBLICATIONS

Anonymous, MethyiEasy DNA Bisulfate Modification Kit- User Guide for Research Use Only, No Date, 24 pages, Human Genetic Signature Ply Ltd. Australia, www.geneticsignatures.com.

Bacolla et al., Recombinant Human DNA (cytosine-5) Methyltransferase, The Journal of Biological Chemistry, Nov. 12, 1999, pp. 33011-33019, vol. 274, No. 46, The American Society for Biochemistry and Molecular Biology, Inc.

Baskaran W., et al., "Uniform Amplification of a Mixture of Deoxyribonucleic Acids with Varying GC Content," Genome Res. vol. 6, No. 7, pp. 633-638, Cold Spring Harbor Laboratory Press (1996).

Brookes., et al., "Cloning the Shared Components of Complex DNA Resources," Human Molecular Genetics, vol. 3, No. 11, pp. 2011-2017 (1994).

Broude et al., "Multiplex Allele-Specific Target Amplification Based on PCR Suppression," PNAS, vol. 98, No. 1, pp. 206-211 (Jan. 2001).

Broude et al., "Stem-loop oligonucleotides: a robust tool for molecular biology and biotechnology", Trends in Biotechnolology, vol. 20, No. 6, Jun. 2002, 249-256.

Brownie J., et al., "The Elimination of Primer-Dimer Accumulation in PCR," Nucleic Acids Research, Oxford University Press, vol. 25, No. 16, pp. 3235-3241 (1997).

Chamberlain J., et al., "Deletion Screening of the Duchenne Muscular Dystrophy Locus via Multiplex DNA Amplification", Nucleic Acids Research, vol. 16, No. 23, 1988, pp. 11141-11156.

Eurogenetic, Quantitative and Qualitative PCR Technology: All Types of Probes and Related Expertise in One Company: pp. 1-47 (2002).

(56) References Cited

OTHER PUBLICATIONS

Fan et al., "Parallel Genotyping of Human SNP's Using Generic High-Density Oligonucleotide Tag Arrays," Genome Research, vol. 10, pp. 853-860, (2000).
Fisher et al., Characterization of cytosine methylated regions and 5-cytosine DNA methyltransferase (Ehmeth) in the protozoan parasite Entamoeba histolytica, Nucleic Acids Research, 2004, pp. 287-297, vol. 32, No. 1, Oxford University Press.
Frigola et al., "Differential DNA hypermethylation and hypomethylation signatures in cancer," Human Molecular Genetics, 2005, pp. 319-326, vol. 14, No. 2, Oxford University Press.
Frigola et al., Methylome profiling of cancer cells by amplification of inter-methylated sites {AIMS}, Nucleic Acids Research, 2002, vol. 30, No. 7, e28, Oxford University Press.
Fukasawa et al. Journal of Human Genetics 2006; 51: 368-374 (Year: 2006).
Gao et al., "DNA microarray: a high throughput approach for methylation detection," Colloids and Surfaces B: Biointerfaces, 2005, pp. 127-131, vol. 40, No. 3, Elsevier.
Gitan et al., "Methylation-Specific Oligonucleotide Microarray: A New Potential for High-Throughput Methylation Analysis," Genome Research, 2002, pp. 158-164, vol. 12, Issue 1, Cold Spring Harbor Laboratory Press.
Gowher et al., Enzymatic Properties of Recombinant Dnmt3a DNA Methyltranferase from Mouse: The Enzyme Modifies DNA in a Non-processive Manner and also Methylates Non-CpA Sites, Journal of Molecular Biology, 2001, pp. 1201-1208, vol. 309, Academic Press.
Henegariu et al., "Multiplex PCR: Critical Parameters and Step-By-Step Protocol", Biotechniques, vol. 23, No. 3, Sep. 1997, pp. 504-511.
http://www.bu.edu/research/Features/sciocoalition.sub.--01/twist.html "A New Twist on a Powerful Theme," (Oct. 31, 2002).
http://www.bu.edu/research/Features/sciocoalition.sub.--01/twist2.html "Return to a New Twist," (Oct. 31, 2002).
http://www.dxsgenotyping.com/technology.sub.--main.html "Scorpions.TM. Technology for PCR Analysis," (Oct. 31, 2002).
http://www.eurogentec.be/code/en/thec.sub.--real.sub.--scor.html "Scorpions.TM. Genomics Oligonucleotides Synthesis," (Oct. 31, 2002).
http://http://www.info.med.yale.edu/genetics/ward/tavi/Guide.html "PCR and Multiplex PCR Guide," (Oct. 31, 2002).
http://http://www.info.med.yale.edu/genetics/ward/tavi/p01.html "PCR Generalities," (Oct. 31, 2002).
http://www.info.med.yale.edu/genetics/ward/tavi/p02.html "Choosing/Designing PCR Primers," (Oct. 31, 2002).
http://www.info.med.yale.edu/genetics/ward/tavi/p04.html "Multiplexing Primer Pairs," (Oct. 31, 2002).
http://www.mdlab.com/fees&servs/serv-polymerase.html "Medical Diagnostic Laboratories Diagnostic Services: Application of the Polymerase Chain Methodologies in Molecular Diagnostic Medicine," (Oct. 31, 2002).
http://www.medprobe.com/no/rtper.html "MedProbe: Real Time PCR Products and Instruments," (Oct. 31, 2002).
http://www.biagen.com/clinical/applications/technologies/multiplex.sub.--p--cr.asp "Molecular Diagnostics Research and Clinical Research," (Oct. 31, 2002).
http://www4.amershambiosciences.com/aptrix/upp01077.nsf/Content/gel.sub.--blot.sub.--fluor.sub.--imaging.html "Multiplex PCR Product Analysis: Increased Accuracy and Throughput," (Oct. 31, 2002).
Kebelmann-Betzing et al., "Advantages of a New Taq DNA Polymerase in Multiplex PCR and Time-Release PCR," Biotechniques, vol. 24, No. 1, pp. 154-158 (1998).
Larijani et al., "Methylation protects cytidines from AID-mediated deamination," Molecular Immunology, 2005, pp. 599-604, vol. 42, Elsevier.
Lewin, The Mystiques of Epigenetics, Cell, May 1, 1998, pp. 301-303, vol. 93, Cell Press.
Lippman et al., Role of transposable elements in heterochromatin and epigenetic control, Nature, Jul. 22, 2004, pp. 471-476, vol. 430, Nature Publishing Group.
Lizardi et al. Mutation detection and single-molecule counting using isothermal rolling-circle amplification. Nature Genetics 19 (1998) 225-232.
Markoulatos et al., "Multiplex Polymerase Chain Reaction: A Practical Approach," J. Clin. Lab. Anal, vol. 16, pp. 47-51 (2002).
Oakeley, DNA methylation analysis: a review of current methodlogies, Pharmacology & Therapeutics, 1999, pp. 389-400, vol. 84, Elsevier.
Peale F., et al., "Multiplex Display Polymerase Chain Reaction Amplifies and Resolves Related Sequences Sharing a Single Moderately Conserved Domain" Anal Biochem, vol. 256, No. 2, pp. 158-168, (1998).
Pradhan et al., Mammilian DNA {cytosine-5} methyltransferases and their expression, Clinical Immunology, 2003, pp. 6-16, vol. 109, Academic Press.
Pradhan et al., Recombinant Human DNA {Cytosine-5} methyltransferase, The Journal of Biological Chemistry, Nov. 12, 1999, 33002-33010, vol. 274, No. 46, the American Society for Biochemistry.
Rauch et al., "Methylated-CpG island recovery assay: a new technique for the rapid detection of methylated-CpG islands in cancer," Laboratory Investigation, 2005, pp. 1-9.
Sadri et al., Rapid analysis of DNA methylation using new restriction enzyme sites created by bisulfite modification, Nucleic Acids Research, 1996, pp. 5058-5059, vol. 24, No. 24, Oxford University Press.
Shoemaker et al., "Quantitative Phenotypic Analysis of Yeast Deletion Mutants Using a Highly Parallel Molecular Bar-Coding Strategy," Nature Genetics, vol. 14, No. 4, Dec. 1996, pp. 450-456.
Tatusova et al., "Blast 2 Sequences—A New Tool for Comparing Protein and Nucleotide Sequences," Fems Microbiology Letters, vol. 174, pp. 247-250 (1999).
Testa et al. Chip on chip experiments uncover a widespread distribution of NF-Y binding CCAAT sites outside of Core promoters, J. Bioi. Chern., Jan. 11, 2005, Manuscript M414039200, The American Society for Biochemistry and Molecular Biology, Inc.
Thelwell et al., "Mode of Action and Application of Scorpion Primers to Mutation Detection," Nucleic Acids Research, vol. 28, No. 19, pp. 3752-3761 (2000).
Thomassin, Helene et al.; "MethylQuant: a sensitive method for quantifying methylation of specific cytosines within the genome"; Nucleic Acids Research (2004); vol. 32, No. 21; pp. 1-9.
Tompa et al., Genome-Wide Profiling of DNA Methylation Reveals Transposon Targets of CHROMOMETHYLASE3, Current Biology, Jan. 8, 2002, pp. 65-68, vol. 12, Elseveir.
Toyota, Minoru et al.; "Identification of Differentialy Methylated Sequences in Colorectal Cancer by Methylated CpG Island Amplification"; Cancer Research 59; May 15, 1999; pp. 2307-2312.
Wang et al., Balanced-PCR amplification allows unbiased identification of genomic copy changes in minute cell and tissue samples, Nucleic Acids Research, 2004, vol. 32, No. 9, e76, Oxford University Press.
Wang et al., DNA amplification method tolerant to sample degradation, Genome Research, 2004, pp. 2357-2366, vol. 14, Cold Spring Harbor Laboratory Press.
Whitcombe et al., "Detection of PCR Products Using Self-Probing Amplicons and Fluorescence," Nature Biotechnology, Aug. 1999, vol. 17(8), pp. 804-807.
Xiong et al., COBRA; a sensitive and quantitative DNA methylation assay, Nucleic Acid Research, 1997, pp. 2532-2534, vol. 25, No. 12, Oxford University Press.
Yan et al., "Applications of CpG island microarrays for high-throughput analysis of DNA methylation," J. Nutr., 132(8 Suppl): 2430S-2434S (Aug. 2002).
Yan et al., "Use of CpG island microarrays to identify colorectal tumors with a high degree of concurrent methylation," Methods, 27(2):162-9 (Jun. 2002).
Zangenberg et al., "Improved Multiplex PCR of Plymorphic Markers," http://www.promega.com/geneticidproc/ussymp7proc/ab73.html (Oct. 31, 2002).

\* cited by examiner

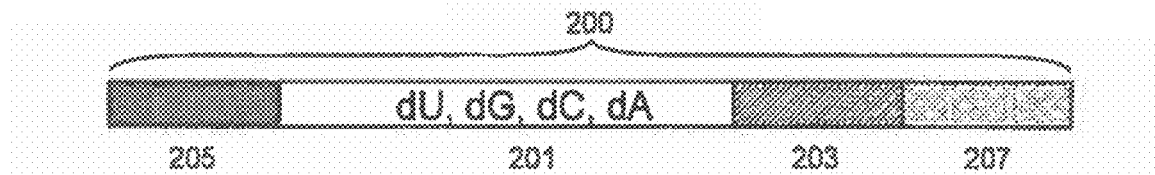
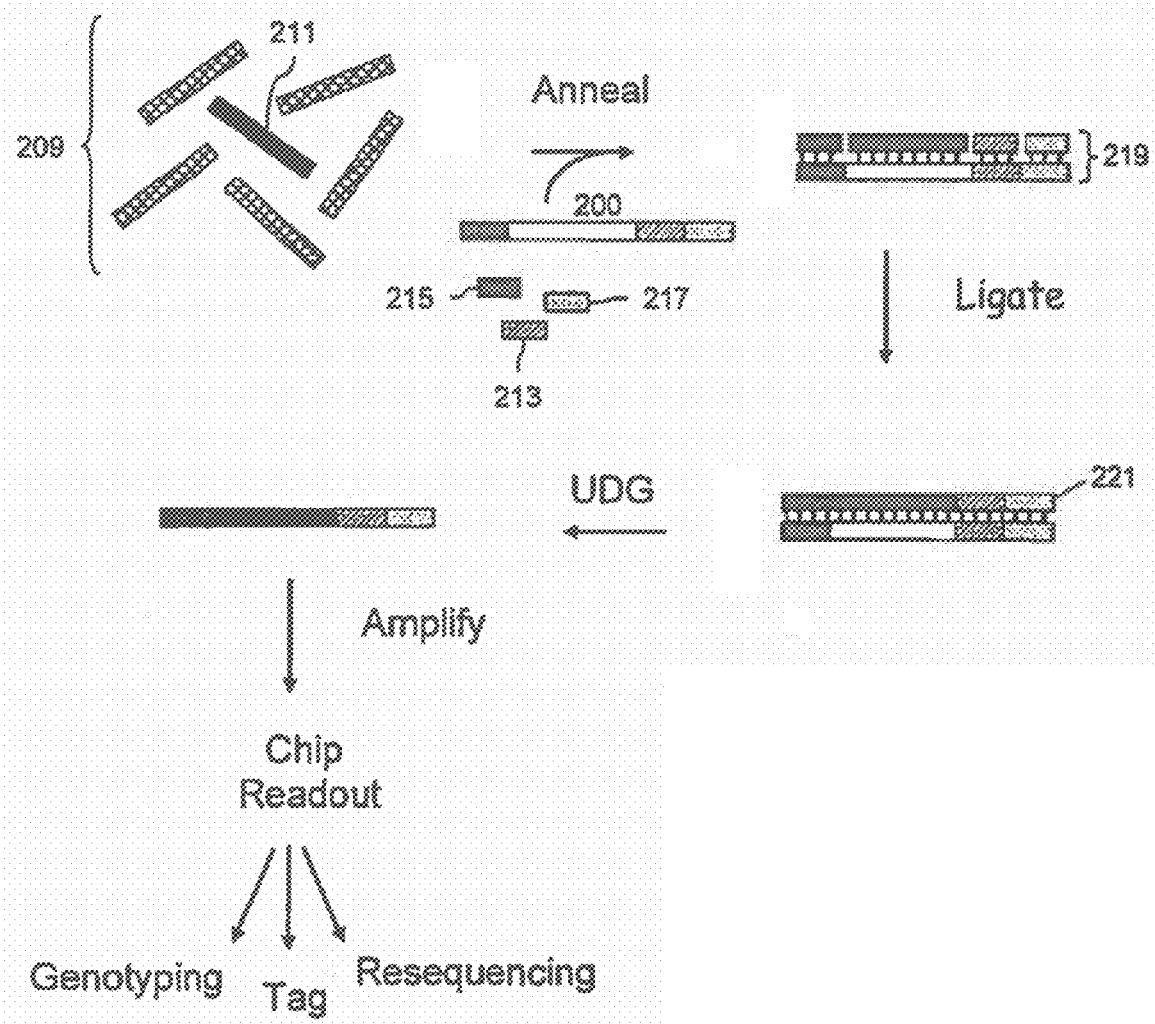

FIG 4

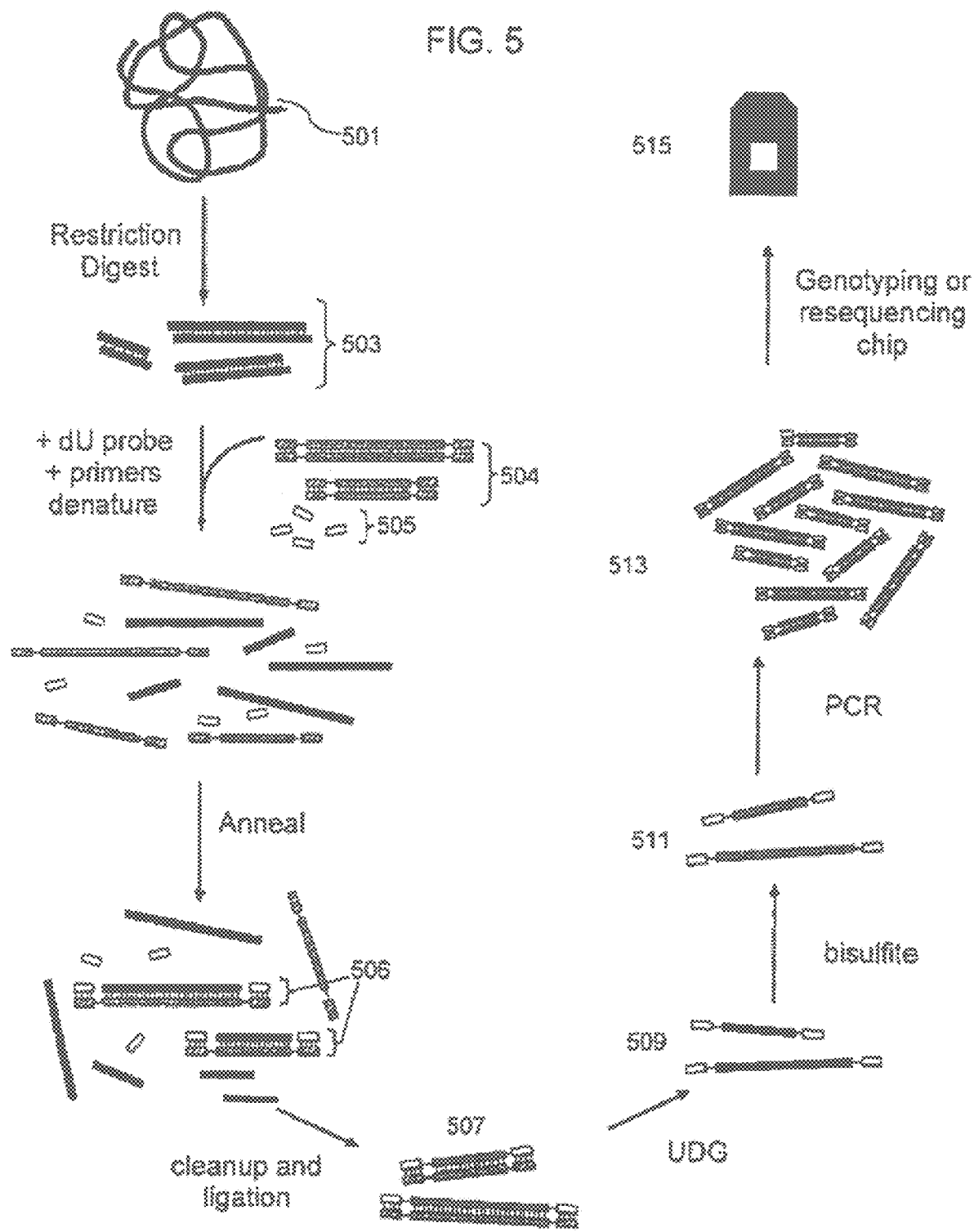

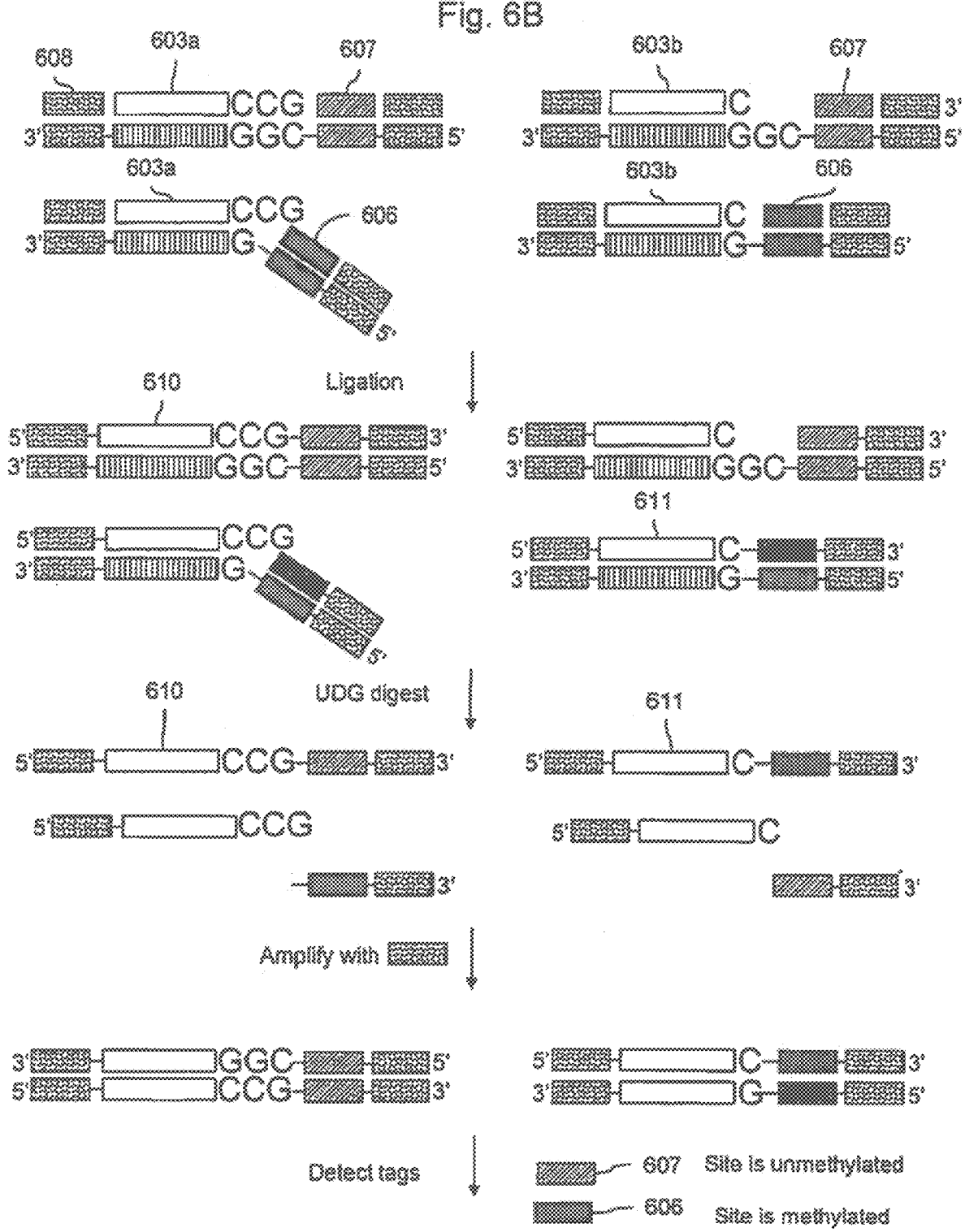

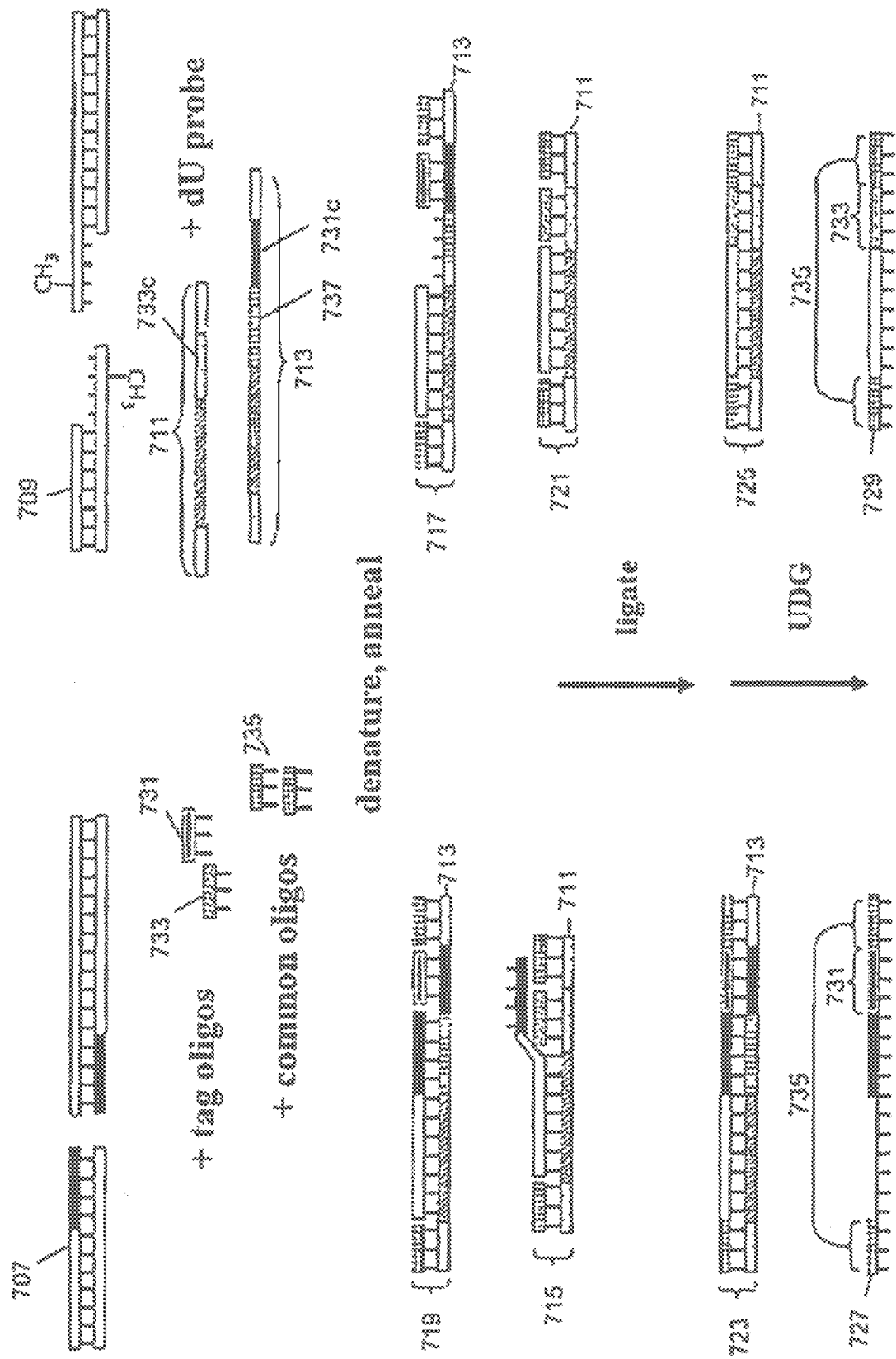

METHODS OF ANALYSIS OF METHYLATION

RELATED APPLICATIONS

The present application is a divisional application of U.S. application Ser. No. 15/281,721, filed Sep. 30, 2016 which issued as U.S. Pat. No. 10,407,717 on Sep. 10, 2019, which is a divisional application of U.S. application Ser. No. 11/923,649, filed Oct. 24, 2007 and now abandoned, which claims the benefit of U.S. Provisional Application No. 60/862,735, filed Oct. 24, 2006, and is a continuation-in-part application of U.S. application Ser. No. 11/739,654, filed Apr. 24, 2007, now U.S. Pat. No. 7,754,451, which is a continuation application of U.S. application Ser. No. 10/300,311, filed Nov. 19, 2002, now U.S. Pat. No. 7,208,295, which claims the benefit of U.S. Provisional Application No. 60/331,693, filed Nov. 19, 2001, the disclosure of the above applications are incorporated herein by reference in their entireties.

BACKGROUND OF THE INVENTION

The genomes of higher eukaryotes contain the modified nucleoside 5-methyl cytosine (5-meC). This modification is usually found as part of the dinucleotide CpG. Cytosine is converted to 5-methylcytosine in a reaction that involves flipping a target cytosine out of an intact double helix and transfer of a methyl group from S-adenosylmethionine by a methyltransferase enzyme (Klimasauskas et al., *Cell* 76:357-369, 1994). This enzymatic conversion is the only epigenetic modification of DNA known to exist in vertebrates and is essential for normal embryonic development (Bird, *Cell* 70:5-8, 1992; Laird and Jaenisch, *Human Mol. Genet.* 3:1487-1495, 1994; and Li et al., *Cell* 69:915-926, 1992).

The frequency of the CpG dinucleotide in the human genome is only about 20% of the statistically expected frequency, possibly because of spontaneous deamination of 5-meC to T (Schoreret et al., *Proc. Natl. Acad Sci. USA* 89:957-961, 1992). There are about 28 million CpG doublets in a haploid copy of the human genome and it is estimated that about 70-80% of the cytosines at CpGs are methylated. Regions where CpG is present at levels that are approximately the expected frequency are referred to as "CpG islands" (Bird, A. P., *Nature* 321:209-213, 1986). These regions have been estimated to comprise about 1% of vertebrate genomes and account for about 15% of the total number of CpG dinucleotides. CpG islands are typically between 0.2 and 1 kb in length and are often located upstream of housekeeping and tissue-specific genes. CpG islands are often located upstream of transcribed regions, but may also extend into transcribed regions. About 2-4% of cytosines are methylated and probably the majority of cytosines that are 5' of Gs are methylated. Most of the randomly distributed CpGs are methylated, but only about 20% of the CpGs in CpG islands are methylated. Recent studies on CpG islands suggest that promoters segregate into two classes by CpG content. See, Saxonov et al., *PNAS* 103(5):1412-7 (2006).

DNA methylation is an epigenetic determinant of gene expression. Patterns of CpG methylation are heritable, tissue specific, and correlate with gene expression. The consequence of methylation is usually gene silencing. DNA methylation also correlates with other cellular processes including embryonic development, chromatin structure, genomic imprinting, somatic X-chromosome inactivation in females, inhibition of transcription and transposition of foreign DNA and timing of DNA replication. When a gene is highly methylated it is less likely to be expressed, possibly because CpG methylation prevents transcription factors from recognizing their cognate binding sites. Proteins that bind methylated DNA may also recruit histone deacetylase to condense adjacent chromatin. Such "closed" chromatin structures prevent binding of transcription factors. Thus the identification of sites in the genome containing 5-meC is important in understanding cell-type specific programs of gene expression and how gene expression profiles are altered during both normal development and diseases such as cancer. Precise mapping of DNA methylation patterns in CpG islands has become essential for understanding diverse biological processes such as the regulation of imprinted genes, X chromosome inactivation, and tumor suppressor gene silencing in human cancer caused by increase methylation.

Methylation of cytosine residues in DNA plays an important role in gene regulation. Methylation of cytosine may lead to decreased gene expression by, for example, disruption of local chromatin structure, inhibition of transcription factor-DNA binding, or by recruitment of proteins which interact specifically with methylated sequences and prevent transcription factor binding. DNA methylation is required for normal embryonic development and changes in methylation are often associated with disease. Genomic imprinting, X chromosome inactivation, chromatin modification, and silencing of endogenous retroviruses all depend on establishing and maintaining proper methylation patterns. Abnormal methylation is a hallmark of cancer cells and silencing of tumor suppressor genes is thought to contribute to carcinogenesis. Methylation mapping using microarray-based approaches may be used, for example, to profile cancer cells revealing a pattern of DNA methylation that may be used, for example, to diagnose a malignancy, predict treatment outcome or monitor progression of disease. Methylation in eukaryotes can also function to inhibit the activity of viruses and transposons, see Jones et al., *EMBO J.* 17:6385-6393 (1998). Alterations in the normal methylation process have also been shown to be associated with genomic instability (Lengauer et al., *Proc. Natl. Acad. Sci. USA* 94:2545-2550, 1997). Such abnormal epigenetic changes may be found in many types of cancer and can serve as potential markers for oncogenic transformation.

SUMMARY OF THE INVENTION

Methods for analyzing the methylation status of cytosines in genomic DNA are disclosed.

In some aspects the methods include a step of multiplex amplification of a plurality of regions of interest. The methods provide for the addition of known priming sequences to the 5' and 3' ends of the sequences to be amplified so that subsequent amplification may be performed using primers to the known priming sequences. Such multiplexed amplification reactions provide high specificity and uniform amplification of templates.

In a first aspect, the invention provides a method for multiplex locus specific amplification of a plurality of templates to provide a plurality of templates with known 5' and 3' ends.

The template may be derived from cDNA or genomic DNA, from a single individual or from a plurality of individuals. The template may, for example, be genomic DNA derived from a eukaryote, such as a human being.

The multiplex methods of the present invention may include at least 10 templates of distinct sequence, at least 100 templates of distinct sequence, at least 1000 templates of distinct sequence, or more. Usefully, at least one of the first and second oligonucleotides comprises a bar code sequence, thus allowing concurrent detection of all amplified templates.

In one embodiment, genomic DNA is modified by bisulfite. Fragments of the modified DNA are generated with defined ends using locus specific primer extension. The extension products have defined ends and are then hybridized to a dU probe and adaptor sequences are ligated to the ends. The dU probe is degraded and the adaptor ligated fragments are amplified.

In some aspects the methods are used to classify a tissue into a class, for example, a known tumor class. The hybridization pattern obtained from the tissue sample, using the disclosed methods, is compared to hybridization patterns from samples from tissues of known tumor class, obtained using the disclosed methods.

In one aspect a method for analyzing the methylation of a plurality of cytosines in a plurality of target sequences is disclosed. A a genomic DNA sample is fragmented to generate fragments that include a mixture of target fragments and non-target fragments. The fragments are mixed with a common primer sequence and a collection of dU probes that are complementary to different target sequences to be analyzed. Each dU probe has a sequence that is complementary to a different target fragment flanked at both ends by the complement of the common primer sequence. Target fragments and common primer sequences hybridize to dU probes to form ligation complexes and ligase is added to ligate the common primer sequences to the target fragments in the ligation complexes. The dU probes are digested using UDG and the ligated products are treated with bisulfite and amplified. The amplification product is analyzed, for example, by hybridization to an array to determine the methylation state of cytosines in the starting sample by detecting sequence changes corresponding to bisulfite modification.

In another aspect DNA is fragmented with a methylation sensitive enzyme so that only unmethylated DNA is fragmented. The overhang created by cleavage is filled in with a DNA polymerase, marking the unmethylated fragments with an additional sequence. The DNA is then fragmented with an isoschizomer of the first enzyme that is methylation insensitive so it will cleave the methylated sites. The fragments are then hybridized to dU probes that are designed to hybridize to either the fragment generated by cleavage then filling or cleavage alone. Amplification products are generated that are differentially detectable, for example, by being marked with different tag sequences.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which:

In FIG. 1A a template with defined ends is obtained by primer extension. In FIG. 1B common sequences are ligated to the ends of the template. FIG. 1C shows an alternate embodiment for digestion of the template probe.

FIG. 2A illustrates one embodiment of a dU probe.

FIG. 2B illustrates the use of dU probes for multiplex amplification of specific target sequences from a complex sample.

FIG. 4 shows the changes resulting from treatment of DNA with bisulfite followed by PCR amplification.

FIG. 5 illustrates a method of using dU probes in combination with bisulfite treatment for methylation analysis.

FIG. 6A-6B are schematic representations illustrating a method for determining if a restriction site is methylated. FIG. 6A illustrates methyl sensitive digestion and hybridization of methylation specific dU probes. FIG. 6B shows how differentially tagged fill-in and non fill specific dU probes are used to detect presence or absence of methylation.

FIG. 7A-7C show a method for determining methylation state of a restriction site using dU probes. FIG. 7A shows differential cleavage and end filling steps for determining methylation using dU probes that distinguish between methylated and unmethylated restriction sites.

FIG. 7B shows differential dU probes as template for ligation of tags and primers to different cleavage products from FIG. 7A.

FIG. 7C shows a schematic and a gel image of fragments resulting from restriction enzyme cleavage, dU probe hybridization and template directed ligation, followed by PCR amplification of 9 targets.

DETAILED DESCRIPTION OF THE INVENTION

General

Figure 1A:
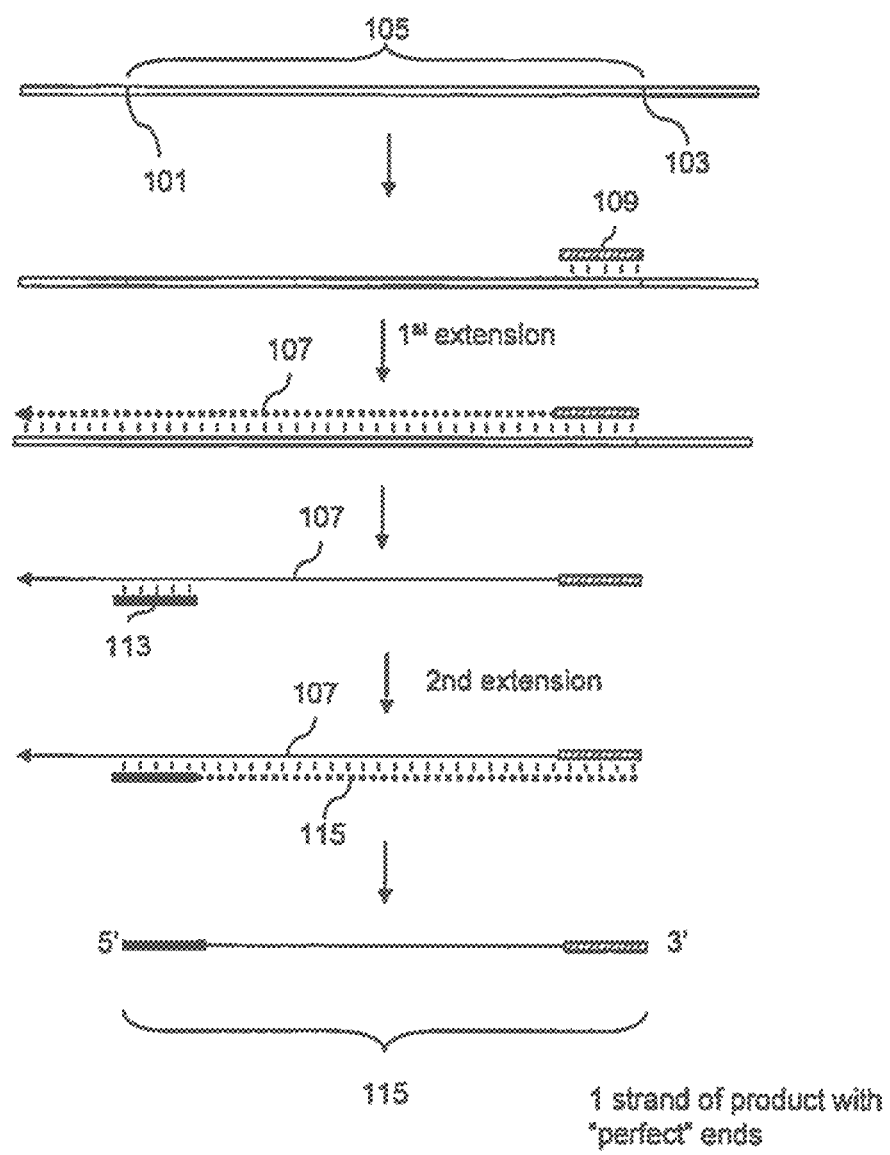
FIG. 1A-1C are a schematic representation illustrating methods for appending known sequences to a single-stranded nucleic acid template at specific positions.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being, but may also include other organisms including but not limited to mammals, plants, fungi, bacteria or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, *IRL Press, London*, Nelson and Cox (2000), Lehninger, *Principles of Biochemistry* 3$^{rd}$ Ed., W.H. Freeman Pub., New York, N.Y. and Berg et al. (2002) *Biochemistry*, 5$^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with hybridization to an array, the sample may be amplified by a variety of mechanisms, some of which may employ PCR. See, for example, PCR Technology: *Principles and Applications for DNA Amplification* (Ed. H. A. Erlich, Freeman Press, NY, NY, 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159, 4,965,188, and 5,333,675. The sample may be amplified on the array. See, for example, U.S. Pat. No. 6,300,070 which is incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245), rolling circle amplification (RCA) (for example, Fire and Xu, *PNAS* 92:4641 (1995) and Liu et al., *J. Am. Chem. Soc.* 118:1587 (1996)) and nucleic acid based sequence amplification (NABSA), (See, U.S. Pat. Nos. 5,409,818, 5,554,517, and 6,063,603). Other amplification methods that may be used are described in, U.S. Pat. Nos. 5,242,794, 5,494,810, 4,988,617 and in U.S. Ser. No. 09/854,317. Other amplification methods are also disclosed in Dahl et al., *Nuc. Acids Res.* 33(8):e71 (2005) and circle to circle amplification (C2CA) Dahl et al., *PNAS* 101:4548 (2004). Locus specific amplification and representative genome amplification methods may also be used.

Additional methods of sample preparation and techniques for reducing the complexity of a nucleic sample are described in Dong et al., *Genome Research* 11, 1418 (2001), in U.S. Pat. Nos. 6,872,529, 6,361,947, 6,391,592 and 6,107,023, US Patent Publication Nos. 20030096235 and 20030082543 and U.S. patent application Ser. No. 09/916,135.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2$^{nd}$ Ed. Cold Spring Harbor, N.Y, 1989); Berger and Kimmel *Methods in Enzymology*, Vol. 152, *Guide to Molecular Cloning Techniques* (Academic Press, Inc., San Diego, Calif., 1987); Young and Davism, *P.N.A.S,* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Ser. Nos. 10/389, 194, 60/493,495 and in PCT Application PCT/US99/06097 (published as WO 99/47964), each of which also is hereby incorporated by reference in its entirety for all purposes. Instruments and software may also be purchased commercially from various sources, including Affymetrix.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2$^{nd}$ ed., 2001). See U.S. Pat. No. 6,420,108.

Methods for detection of methylation status are disclosed, for example, in Fraga and Esteller, *BioTechniques* 33:632-649 (2002) and Dahl and Guldberg Biogerontology 4:233-250 (2003). Methylation detection using bisulfite modification and target specific PCR have been disclosed, for example, in U.S. Pat. Nos. 5,786,146, 6,200,756, 6,143,504, 6,265,171, 6,251,594, 6,331,393, and 6,596,493. U.S. Pat. No. 6,884,586 disclosed methods for methylation analysis using nicking agents and isothermal amplification.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/197,621, 10/063,559 (United States Publication No. 20020183936), Ser. Nos. 10/065,856, 10/065, 868, 10/328,818, 10/328,872, 10/423,403, and 60/482,389.

All documents, i.e., publications and patent applications, cited in this disclosure, including the foregoing, are incorporated by reference herein in their entireties for all purposes to the same extent as if each of the individual documents were specifically and individually indicated to be so incorporated by reference herein in its entirety.

Definitions

"Adaptor sequences" or "adaptors" are generally oligonucleotides of at least 5, 10, or 15 bases and preferably no more than 50 or 60 bases in length; however, they may be even longer, up to 100 or 200 bases. Adaptor sequences may be synthesized using any methods known to those of skill in the art. For the purposes of this invention they may, as options, comprise primer binding sites, recognition sites for endonucleases, common sequences and promoters. The adaptor may be entirely or substantially double stranded or entirely single stranded. A double stranded adaptor may comprise two oligonucleotides that are at least partially complementary. The adaptor may be phosphorylated or unphosphorylated on one or both strands.

Adaptors may be more efficiently ligated to fragments if they comprise a substantially double stranded region and a short single stranded region which is complementary to the single stranded region created by digestion with a restriction enzyme. For example, when DNA is digested with the restriction enzyme EcoRI the resulting double stranded fragments are flanked at either end by the single stranded overhang 5'-AATT-3', an adaptor that carries a single stranded overhang 5'-AATT-3' will hybridize to the fragment through complementarity between the overhanging regions. This "sticky end" hybridization of the adaptor to the fragment may facilitate ligation of the adaptor to the fragment but blunt ended ligation is also possible. Blunt ends can be converted to sticky ends using the exonuclease activity of the Klenow fragment. For example when DNA is digested with PvuII the blunt ends can be converted to a two base pair overhang by incubating the fragments with Klenow in the presence of dTTP and dCTP. Overhangs may also be converted to blunt ends by filling in an overhang or removing an overhang.

Methods of ligation will be known to those of skill in the art and are described, for example in Sambrook et at. (2001) and the New England BioLabs catalog both of which are incorporated herein by reference for all purposes. Methods include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; *E. coli* DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3'→5' phosphodiester bond, substrates include single-stranded RNA and DNA as well as dinucleoside pyrophosphates; or any other methods described in the art. Fragmented DNA may be treated with one or more enzymes, for example, an endonuclease, prior to ligation of adaptors to one or both ends to facilitate ligation by generating ends that are compatible with ligation.

Adaptors may also incorporate modified nucleotides that modify the properties of the adaptor sequence. For example, phosphorothioate groups may be incorporated in one of the adaptor strands. A phosphorothioate group is a modified phosphate group with one of the oxygen atoms replaced by a sulfur atom. In a phosphorothioated oligo (often called an "S-Oligo"), some or all of the internucleotide phosphate groups are replaced by phosphorothioate groups. The modified backbone of an S-Oligo is resistant to the action of most exonucleases and endonucleases. Phosphorothioates may be incorporated between all residues of an adaptor strand, or at specified locations within a sequence. A useful option is to sulfurize only the last few residues at each end of the oligo. This results in an oligo that is resistant to exonucleases, but has a natural DNA center.

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "epigenetic" as used herein refers to factors other than the primary sequence of the genome that affect the development or function of an organism, they can affect the phenotype of an organism without changing the genotype. Epigenetic factors include modifications in gene expression that are controlled by heritable but potentially reversible changes in DNA methylation and chromatin structure. Methylation patterns are known to correlate with gene expression and in general highly methylated sequences are poorly expressed.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

Restriction enzymes or restriction endonucleases and their properties are well known in the art. A wide variety of restriction enzymes are commercially available, from, for example, New England Biolabs. Restriction enzymes recognize a sequence specific sites (recognition site) in DNA. Typically the recognition site varies from enzyme to enzyme and may also vary in length. Isoschizomers are enzymes that share the same recognition site. Restriction enzymes may cleave close to or within their recognition site or outside of the recognition site. Often the recognition site is symmetric because the enzyme binds the double stranded DNA as homodimers. Recognition sequences may be continuous or may be discontinuous, for example, two half sites separated by a variable region. Cleavage can generate blunt ends or short single stranded overhangs.

In preferred aspects of the present invention enzymes that include at least one CpG dinucleotide in the recognition site may be used. Enzymes with a recognition site that includes the sequence CCGG include, for example, Msp I, Hpa II, Age I, Xma I, Sma I, NgoM IV, Nae I, and BspE I. Enzymes with a recognition site that includes the sequence CGCG include, for example, BstU I, Mlu I, Sac II, BssH II and Nru I. Enzymes with a recognition site that includes the sequence GCGC include, for example, Hin P1 I, Hha I, Afe I, Kas I, Nar I, Sfo I, Bbe I, and Fsp I. Enzymes with a recognition site that includes the sequence TCGA include, for example, Taq I, Cla I, BspD I, PaeR7 I, Tli I, Xho I, Sal I, and BstB I. For additional enzymes that contain CpG in the recognition sequence. See, for example, the New England Biolabs catalog and web site. In some aspects two restriction enzymes may have a different recognition sequence but generate identical overhangs or compatible cohesive ends. For example, the overhangs generated by cleavage with Hpa II or Msp I can be ligated to the overhang generated by cleavage with Taq I. Some restriction enzymes that include CpG in the recognition site are unable to cleave if the site is methylated, these are methylation sensitive. Other enzymes that contain CpG in their recognition site can cleave regardless of the presence of methylation, these are methylation insensitive. Examples of methylation insensitive enzymes, that include a CpG in the recognition site, include BsaW I (WCCGGW), BsoB I, BssS I, Msp I, and Taq I. Examples of methylation sensitive enzymes, that include a CpG in the recognition site, include Aat II, Aci I, Acl I, Afe I, Age I, Asc I, Ava I, BmgB I, BsaA I, BsaH I, BspD I, Eag I, Fse I, Fau I, Hpa II, HinP1 I, Nar I, and SnaB I.

The terms "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

"Specific binding" refers to the ability of two molecular species concurrently present in a heterogeneous (inhomogeneous) sample to bind to one another in preference to binding to other molecular species in the sample. Typically, a specific binding interaction will discriminate over adventitious binding interactions in the reaction by at least two-fold, more typically by at least 10-fold, often at least 100-fold. Typically, the affinity or avidity of a specific binding reaction is least about $10^7$ $M^{-1}$, using at least 108 $M^{-1}$ to at least about $10^9$ $M^{-1}$, and often greater, including affinities or avidities up to $10^{10}$ $M^{-1}$ to $10^{12}$ $M^{-1}$.

Methods for Multiplexed Capture of Genomic DNA

Many of the embodiments described below for analysis of methylation employ methods of capturing a population of pre-selected target sequences from a genomic DNA sample. In some aspects the methods rely on dU probe technology as previously disclosed in US Patent Application No. 20030096291 and U.S. Pat. No. 7,208,295. Additional methods for making and using dU probes are also disclosed in 60/887,546 filed Jan. 31, 2007. Briefly, dU probes may be generated by performing PCR using a pair of primers for each target sequence. Each primer contains a target specific region in the 3' portion and a 5' common sequence. The PCR is performed in the presence of dUTP so uracil is incorporated into the amplification product. The amplicons from different reactions can be pooled and amplified as a single reaction using primers to the common regions in the primers. This results in a pool of dU probes for a collection of target sequences. The pool need only be generated once and aliquots can be used for amplification of the targets from different samples. To use the dU probes an aliquot is mixed with the target sample which has preferably been fragmented to generate ends that are compatible with the target specific region of the dU probes. Sequences complementary to the common regions are also added. The dU probe acts like a splint and the target sequence from the sample is ligated to the common regions and can then be amplified using common primers. These methods allow for amplification of a limited number of specific target sequences from a complex background, for example, 100 to 2,000 different exons of interest from genes of interest or promoter regions of interest can be amplified from human genomic DNA. The sequence of the dU probes determines what sequences will be amplified and variation in the target, for example, polymorphisms that are present in the sample but were not present in the nucleic acid used to generate the dU probes, still allow for amplification of the sequence in the target.

DNA captured by these methods can be used for a variety of purposes, including, for example, methylation analysis, genotyping analysis, resequencing analysis, copy number analysis, haplotype analysis, and variant detection. The captured DNA is ligated to common priming sequences at the 5' and 3' ends of the captured genomic DNA to facilitate amplification. The captured DNA can be treated prior to amplification with the common primers, for example, the DNA can be bisulfite modified to preserve an indication of methylation status. Other treatments are also possible, for example, the captured DNA may be subjected to an affinity separation prior to amplification. For example, 5meC containing captured DNA may be isolated using an antibody to 5meC and one or both fractions may be subsequently amplified.

In preferred aspects, a collection of template probes corresponding to a collection of targets of interest are used as template to facilitate the ligation of common priming sequences to the ends of the target sequences in a nucleic acid sample to be analyzed. After the ligation, the template probes are digested or separated so they are not targets for subsequence amplification. The target sequences can then be amplified from the nucleic acid sample being analyzed and the amplification product can be interrogated.

Each template probe is complementary to a different target of interest flanked by a priming sequence at the 5' end and a second priming sequence at the 3' end. The targets are allowed to hybridize to the corresponding template probe and common priming sequences are ligated to the ends of the target in a subsequent step. The template probes are removed, for example, by digestion and the targets are amplified using primers to the common priming sequences. Non-targets do not have the common priming sequences so they are not amplified. This allows for multiplex amplification of a large number of target sequences, for example, 200 to more than 20,000 selected target sequences from a complex sample such as a genome. The length of each target may be, for example, about 100 to 1000, about 200 to 1000, about 200 to 500, about 200-2000 or about 100 to 5,000 bases. In one embodiment the ends of the targets may be defined by restriction sites in the genomic DNA sequence.

The template probes may also be used to mark the targets with one or more additional sequences. In a particularly preferred embodiment each template probe has a unique barcode sequence between one of the priming sequences and the target complementary region. The target is hybridized to the template probe and oligonucleotides that are complementary to the tags and to the common priming sequences are added and allowed to hybridize to the template. The pieces are hybridized to the template probe so that the ends are juxtaposed and can be ligated to form a contiguous sequence. In some aspects template probes have more than one barcode sequence. The barcode sequence can be used as a unique identifier of subsequent products.

The template probes are synthesized so that the target complementary region has defined ends. The genomic DNA sample from which targets are to be amplified is treated so that the targets have defined ends that correspond to the template probes. This can be accomplished in a variety of ways, for example, the ends may be generated by restriction enzyme digestion or by PCR.

One method for obtaining target sequences with defined ends is illustrated in FIG. 1A, in which a selected target sequence 105 with defined end bases at 101 and 103 is amplified from a larger sequence using locus specific primer extension. The resulting template 120 has ends that are defined by the sequence of oligonucleotide primers 109 and 113. The 5' end of 109 corresponds to position 103 and the 5' end of primer 113 corresponds to position 101. In some embodiments the starting DNA is bisulfite modified genomic DNA.

In the first step of the method, illustrated in FIG. 1A, primer 109 is mixed with the target sequence and extended to form extension product 107. Primer 113 is hybridized to extension product 107 and extended to generate extension product 115 which has the sequence of target 105. A second copy of primer 109 can hybridize to extension product 115 to generate a double stranded fragment.

Figure 1B:
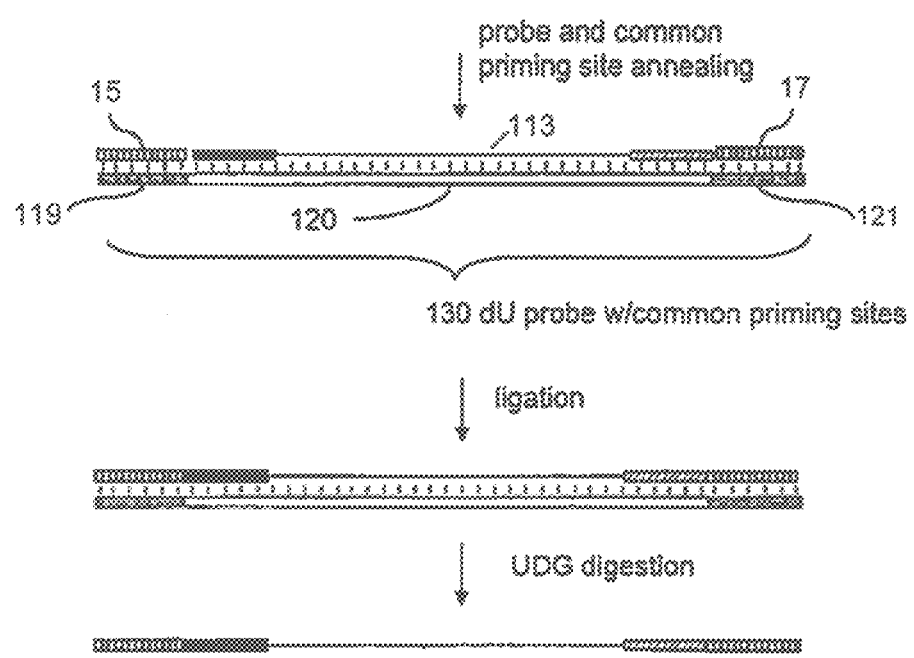

In FIG. 1B single stranded fragment Probe 130 includes at least first target complementarity region 120 and oligonucleotide positioning regions 119 and 121 which are directly adjacent to 120. In the annealing step, template region 113 hybridizes to template complementarity region 120 of probe 130 and oligonucleotide regions 15 and 17 concurrently hybridize to oligonucleotide positioning regions 119 and 121 of probe 130.

The nucleotide of template complementarity region 120 and the nucleotide of oligonucleotide positioning regions 119 and 121 that are directly adjacent within probe 130 define junctions within probe 130, and may be referred to as junctional nucleotides.

In preferred aspects the template probes 130 are synthesized in the presence of dUTP so that U is incorporated into the probe in at least one position and preferably multiple positions. The resulting "dU probes" can be degraded by UDG treatment after they are used as template probes.

Figure 1C:
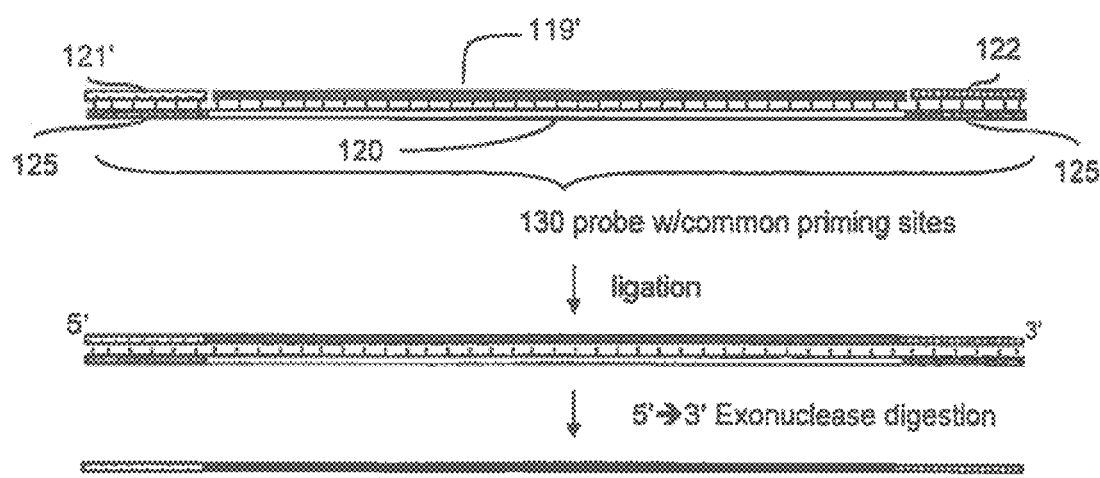

In an alternative embodiment to the dU probe, the template probes need not contain uracil and are degraded by exonuclease treatment instead of by UDG treatment. This embodiment is illustrated in FIG. 1C. In this embodiment the 5' common priming sequence [121'] that is ligated to the 5' end of the genomic target DNA sequence [119'] is resistant to 5' exonuclease activity so the template probe [130] is digested by the exonuclease but the ligated target sequence is not. The targeting region [120] of the probe and the common priming regions [125] of the probe need not have dU incorporated. The sequence may be made exonuclease resistant for example, by inclusion of 4 or 5 phosphorothioate linkages at the 5' end of the oligonucleotide. This has been shown to render oligonucleotides resistant to treatment by T7 exonuclease (Nikiforov, PCR Methods and Applications, 3:285-291, 1994). In another aspect, the 3' oligonucleotide [122] may be resistant to a 3' to 5' exonuclease activity and the template probe [130] may be digested with a 3' to 5' exonuclease activity after capture.

In another aspect STRANDASE X Exonuclease, available from NOVAGEN is used to digest the template probe [130]. This enzyme digests one strand of a DNA duplex from a 5' phosphorylated end. The enzyme can be used to prepare single stranded DNA from PCR products synthesized using one phosphorylated primer and one non-phosphorylated primer. If the 5' end of the template probe [130] is phosphorylated and the 5' end of oligonucleotide 121 is non-phosphorylated STRANDASE λ Exonuclease may be used to degrade the template probe after ligation and prior to amplification.

Methods for Detection of Methylation

Mammalian methylation patterns are complex and change during development, see van Steensel and Henikoff *BioTechniques* 35: 346-357 (2003). Methylation in promoter regions is generally accompanied by gene silencing and loss of methylation or loss of the proteins that bind to the methylated CpG can lead to diseases in humans, for example, Immunodeficiency Craniofacial Syndrome and Rett Syndrome, Bestor (2000) *Hum. Mol. Genet.* 9:2395-2402. DNA methylation may be gene-specific and occurs genome-wide.

Methods for detecting methylation status have been described in, for example U.S. Pat. Nos. 6,214,556, 5,786,146, 6,017,704, 6,265,171, 6,200,756, 6,251,594, 5,912,147, 6,331,393, 6,605,432, and 6,300,071 and US Patent Application publication Nos. 20030148327, 20030148326, 20030143606, 20030082609, 20050153347 and 20050009059, each of which are incorporated herein by reference. Other array based methods of methylation analysis are disclosed in U.S. Patent Publication No. 20050196792 and U.S. patent application Ser. No. 11/213,273 filed Aug. 26, 2005. For a review of selected methylation detection methods, see, Oakeley, E. J., *Pharmacology & Therapeutics* 84:389-400 (1999). Available methods include, but are not limited to: reverse-phase HPLC, thin-layer chromatography, SssI methyltransferases with incorporation of labeled methyl groups, the chloracetaldehyde reaction, differentially sensitive restriction enzymes, hydrazine or permanganate treatment (m5C is cleaved by permanganate treatment but not by hydrazine treatment), sodium bisulfite, combined bisulphate-restriction analysis, and methylation sensitive single nucleotide primer extension.

Other related methods of methylation analysis and arrays that may be useful in conjunction with the disclosed methods include those disclosed in U.S. Provisional Application Nos. 60/744,705 and 60/788,520.

In some embodiments the methods include treatment of the sample with bisulfite. Unmethylated cytosine is converted to uracil through a three-step process during sodium bisulfite modification. The steps are sulphonation to convert cytosine to cytosine sulphonate, deamination to convert cytosine sulphonate to uracil sulphonate and alkali desulphonation to convert uracil sulphonate to uracil. Conversion on methylated cytosine is much slower and is not observed at significant levels in a 4-16 hour reaction. See Clark et al., *Nucleic Acids Res.*, 22(15):2990-7 (1994). If the cytosine is methylated it will remain a cytosine (see FIG. 4). If the cytosine is unmethylated it will be converted to uracil. When the modified strand is copied, through, for example, extension of a locus specific primer, a random or degenerate primer or a primer to an adaptor, a G will be incorporated in the interrogation position (opposite the C being interrogated) if the C was methylated and an A will be incorporated in the interrogation position if the C was unmethylated. When the double stranded extension product is amplified those Cs that were converted to U's and resulted in incorporation of A in the extended primer will be replaced by Ts during amplification. Those Cs that were not modified and resulted in the incorporation of G will remain as C. Bisulfite treatment can degrade the DNA making it difficult to amplify. Also the sequence degeneracy resulting from the treatment complicates primer design. The treatment may also result in incomplete desulfonation, depurination and other as yet uncharacterized DNA damage, making downstream processing more challenging. The treatment can also result in preferential amplification of unmethylated DNA relative to methylated DNA. This may be mitigated by increasing the PCR extension time.

Kits for DNA bisulfite modification are commercially available from, for example, Human Genetic Signatures' Methyleasy and Chemicon's CpGenome Modification Kit. See also, WO04096825A1, which describes bisulfite modification methods and Olek et al. *Nuc. Acids Res.* 24:5064-6 (1994), which discloses methods of performing bisulfite treatment and subsequent amplification on material embedded in agarose beads. In one aspect a catalyst such as diethylenetriamine may be used in conjunction with bisulfite treatment, see Komiyama and Oshima, *Tetrahedron Letters* 35:8185-8188 (1994). Diethylenetriamine has been shown to catalyze bisulfite ion-induced deamination of 2'-deoxycytidine to 2'-deoxyuridine at pH 5 efficiently. Other catalysts include ammonia, ethylene-diamine, 3,3'-diaminodipropylamine, and spermine. In some aspects deamination is performed using sodium bisulfite solutions of 3-5 M with an incubation period of 12-16 hours at about 50° C. A faster procedure has also been reported using 9-10 M bisulfite pH 5.4 for about 10 minutes at 90° C., see Hayatsu et al, *Proc. Jpn. Acad. Ser. B* 80:189-194 (2004).

Bisulfite treatment allows the methylation status of cytosines to be detected by a variety of methods. For example, any method that may be used to detect a SNP may be used, for examples, see Syvanen, *Nature Rev. Gen.* 2:930-942 (2001). Methods such as single base extension (SBE) may be used or hybridization of sequence specific probes similar to allele specific hybridization methods. In another aspect the Molecular Inversion Probe (MIP) assay may be used.

In a preferred aspect, molecular inversion probes, described in Hardenbol et al., *Genome Res.* 15:269-275 (2005) and in U.S. Pat. No. 6,858,412, may be used to determine methylation status after methylation dependent modification. A MIP may be designed for each cytosine to be interrogated. In a preferred aspect the MIP includes a locus specific region that hybridizes upstream and one that hybridizes downstream of an interrogation site and can be extended through the interrogation site, incorporating a base that is complementary to the interrogation position. The interrogation position may be the cytosine of interest after bisulfite modification and amplification of the region and the detection can be similar to detection of a polymorphism. Separate reactions may be performed for each NTP so extension only takes place in the reaction containing the base corresponding to the interrogation base or the different products may be differentially labeled.

In one embodiment methods for identifying methylation based on differential cleavage by restriction enzymes are used. Methylation-sensitive restriction analysis followed by PCR amplification or Southern analysis have been disclosed, for example, in Huang et al., *Cancer Res.* 57:1030-1034 (1997), Zuccotti et al, *Methods in Enzym.* 225:557-567 (1993), Carrel et al., *Am Jour. Med. Genet.* 64:27-30 (1996) and Chang et al., *Plant Mol. Bio. Rep.* 10:362-366 (1992).

In some embodiments of the present invention, at least one oligonucleotide is appended to at least 2 templates of distinct sequence, typically at least 5 templates of distinct sequence, even at least 10, 20, 30, 40, or even at least 50 templates of distinct sequence, and may be appended to 100, 500, 1000, even 5000 or more templates of distinct sequence.

Barcode tags are short nucleic acids having sequence that is designed algorithmically to maximize discrimination on a microarray displaying complements of the respective tags; a 1:1 correspondence as between tag sequence and nucleic acid to which it is appended permits each such nucleic acid to be identified by detection of the bar code uniquely associated therewith. See, e.g., Shoemaker et al., *Nature Genet.* 14(4):450-6 (1996); EP 0799897; Fan et al., *Genome Res.* 10:853-60 (2000); and U.S. Pat. No. 6,150,516, the disclosures of which are incorporated herein by reference in their entireties.

In the methods of the present invention, a distinct bar code sequence may be included in each species. In these embodiments, the terminal region of each species of oligonucleotide is distinct in sequence, and can anneal only to a single species of probe. The 1:1 correspondence as between tag sequence and template-appended oligonucleotide thus permits each template or template amplification product to be identified by detection of the barcode uniquely associated therewith.

Appending common first and second priming sites directly to each of the plurality of templates of distinct sequence—without prior amplification of the template—facilitates the subsequent stoichiometric amplification and analysis of a wide variety of templates of distinct sequence, obviating the problems of unequal amplification observed with many multiplex PCR approaches. By permitting the de novo design of the priming sites, independent of considerations of template sequence, the methods of the present invention also permit amplification with primers having optimal hybridization characteristics, decreasing artifacts such as primer dimer formation.

In preferred aspects of the present methods enzymes that include at least one CpG dinucleotide in the recognition site may be used. Enzymes with a recognition site that includes the sequence CCGG include, for example, Msp I, Hpa II, Age I, Xma I, Sma I, NgoM IV, Nae I, and BspE I. Enzymes with a recognition site that includes the sequence CGCG include, for example, BstU I (CGCG, MSRE), Mlu I (ACGCGT, MSRE), Sac II (CCGCGG, MSRE), BssH II (GCGCGC, MSRE) and Nru I (TCGCGA, MSRE). Not I, BstZ I, Csp I and Eag I have two CpG's in their recognition sites and cleavage is blocked by CpG methylation. Enzymes with a recognition site that includes the sequence GCGC include, for example, Hin P1 I, Hha I, Afe I, Kas I, Nar I, Sfo I, Bbe I, and Fsp I. Enzymes with a recognition site that includes the sequence TCGA include, for example, Taq I, Cla I (MSRE), BspD I (MSRE), PaeR7 I, Tli I, Xho I, Sal I, and BstB I. For additional enzymes that contain CpG in the recognition sequence and for information about the enzyme's sensitivity to methylation see, for example, the New England Biolabs catalog and web site. In some aspects two restriction enzymes may have a different recognition sequence but generate identical overhangs or compatible cohesive ends. For example, the overhangs generated by cleavage with Hpa II or Msp I can be ligated to the overhang generated by cleavage with Taq I. Some restriction enzymes that include CpG in the recognition site are unable to cleave if the site is methylated, these are methylation sensitive restriction enzymes (MSRE). Other enzymes that contain CpG in their recognition site can cleave regardless of the presence of methylation, these are methylation insensitive restriction enzymes (MIRE). A third type of enzyme cleaves only when the recognition site is methylated, and are referred to herein as methylation dependent restriction enzymes (MDRE). Examples of MIREss that have a CpG in the recognition sequence include, for example, BsaW I (WCCGGW), BsoB I, BssS I, Msp I, and Taq I. Examples of MSREs, that include a CpG in the recognition site, include Aat II, Aci I, Acl I, Afe I, Age I, Asc I, Ava I, BmgB I, BsaA I, BsaH I, BspD I, Cla I, Eag I, Fse I, Fau I, Hae III, Hpa II, HinP1 I, Mlu I, Nar I, Not I, Nru I, Pvu I, Sac II, Sal I, Sma I and SnaB I. In preferred aspects a pair of enzymes that have differential sensitivity to methylation and cleave at the same recognition sequence. with one member of the pair being a MSRE and the other member being a MIRE is used. Such pairs include, for example, Hpa II (MSRE) and Msp I (MIRE). Both have recognition sequence CCGG. Another pair that may be used is Sma I (MSRE) and Xma I (MIRE). In another aspect the pair is Bis I a MDRE and Fnu4HI a MSRE. Both enzymes recognize the site GCNGC but Bis I cleaves specifically at methylated C within the sequence G(5mC)^NGC [Degtyarev et al., *Izv. Sib. Otd. Akad. Nauk SSSR* 15:25-26 (1989) and Chmuzh et al., *Biotekhnologia* 3:22-26 (2005)], (^ indicates the position of cleavage within the recognition sequence) while cleavage by Fnu4HI at GC^NGC is blocked by methylation. BthCI also cuts at GCNG^C. GlaI is another MDRE recognizing G(5m)C^GC, see Chernukhin et al., SibEnzyme Scientific Library, October 2005. MSREs to pair with GlaI may include, for example, HpaI (GCG^C) and HinP1I (G^CGC). DpnI is another MDRE recognizing G(m6A) ^TC while MboI (^GATC), ChaI (GATC^) and BstKTI (GAT^C) recognize unmethylated GATC sites.

FIG. 2A and FIG. 2B illustrate the use of the dU probe for multiplex amplification. FIG. 2A shows the components of the dU probe [200]. The dU probe has a central targeting region [201] composed of dU, dG, dC and dA, a tag region [203] and two common priming regions, one at the 5' end of the probe [205] and the second at the 3' end of the probe [207]. There is a dU probe for each target to be amplified. Each probe in the collection of dU probes preferably has the same common regions as other probes in the collection, facilitating universal priming for amplification by, for example, PCR. The dU probes differ in the sequence of the targeting region and the tag region, although groups of dU probes may share the same tag region in some aspects.

In FIG. 2B, the dU probes [200] are mixed with the sample [209] from which the targets [211] are to be amplified along with sequences that are complementary to the tag region [213] and to the common regions [215, 217]. The target, tag complements, and common region complements hybridize to the dU probe to form a complex [219]. A ligase is added to ligate the ends of the annealed fragments to form a ligation product [221]. UDG is added to cleave the dU probes and the remaining ligated target [221] containing fragment is amplified. The presence of the fragment may then be detected, for example, by hybridization to an array of probes. In some aspects the array of probes may include probes that are complementary to the tag sequence. In another aspect the array is a genotyping array. In another aspect the array is a resequencing array. In another aspect the array is a copy number array. In another aspect the array is a gene expression array.

Detection of bisulfite converted DNA on arrays is complicated for several reasons. First, the converted sequences are generally AT rich and often have low complexity. Second, because there may be multiple CpGs in a single probe target and each may be methylated or unmethylated there is a combinatorial problem with the number of different possible perfect match probes that may be necessary. For example, if the starting sequence is GACGAACGCGGCT (SEQ ID NO. 9), there are three cytosines that may be methylated or unmethylated. This generates 8 possible outcomes after bisulfite treatment:

GACGAACGCGGCT (SEQ ID NO. 9)

GACGAACGTGGCT (SEQ ID NO. 10)

GACGAATGTGGCT (SEQ ID NO. 11)

GATGAATGTGGCT (SEQ ID NO. 12)

GATGAATGCGGCT (SEQ ID NO. 13)

GATGAACGCGGCT (SEQ ID NO. 14)

GACGAATGCGGCT (SEQ ID NO. 15)

GATGAACGTGGCT (SEQ ID NO. 16)

Each different possible outcome could be targeted by a different perfectly complementary probe. For the 8 possible outcomes there would be 8 different perfect match probes on the array. The probe could be complementary to either strand.

A pilot experiment was performed using the following sequences as target loci (CGs are underlined):

(SEQ ID NO. 17)
AGCTGGTGATGCTGATCAGAGCCTCTGTAGTCTTAAATGACTTTTCTAA

CTAATTCTAAATCTTCAGAACCCATCGTATAAAAAGGCCATACCTTCTG

GAGGGACGTCGATGGTATTAGGATAGAAGCACCAGGGGACCCCACGAAC

GGTGTCGTCGAAACAGCAGCCCTTATTTGCACACTGGGAGGG (SEQ ID NO. 18)
GGGACCACCCTTATAAGGCTCGGAGGCCGCGAGGCCTTCGCTGGAGTTT

CGCCGCCGCAGTCTTCGCCACCAGTGAGTACGCGCGGCCCGCGTCCCCG

GGGATGGGGCTCAGAGCTCCCAGCATGGG (SEQ ID NO. 19)
GCAGGGGAGGGAAGCAGATGCCAGCGGGCCGAAGAGTCGGGAGCCGGAG

CCGGGAGAGCGAAAGGAGAGGGGACCTGGCGGGGCACTTAGGAGCCAAC

CGAGGAGCAGGAGCACGGACTCCCACTGTGGAAAGGAGGACCAGAA

An array was designed to interrogate both forward and reverse strands of the three target loci. For each CpG 21, 23 and 25 base probes were included. For the 21 mers and 23 mers the probes were tiled from −1 to +5 with the central CpG at the central or 0 position. For the 25 mer probes they were tiled from −3 to +3 with the central CpG at 0. If multiple CpGs were present in a probe all combinatorial possibilities were represented on the array. All probes were included with 9 fold redundancy. Completely unmethylated or completely methylated DNA was bisulfite converted (Zymo kit), subjected to locus specific amplification, labeled and hybridized to the array (2 pM or 20 pM). The hybridization conditions were 3M TMAC, 10 mM Tris pH 7.8, 0.01% TWEEN® 20, 0.5 mg/ml BSA, 0.1 mg/ml HS DNA at 49° C. overnight. Low stringency wash conditions were 6×SSPE and 0.1% TWEEN® 20. High stringency wash conditions were 0.6×SSPE and 0.1% TWEEN® 20.

For data analysis only the probes that detect either completely methylated ("C probe signal") or completely unmethylated ("T probe signal") were used since the starting DNA was completely methylated or unmethylated. Two values were plotted: the log signal sum=log (C probe signal+T probe signal) and the signal contrast=(T probe signal−C probe signal)/(C probe signal+T probe signal). For methylated the signal contrast is expect to be −1 (all signals from C probes) and for unmethylated the signal contrast is expected to be 1 (all signal from T probes). Plotting "log sig sum" versus "sig contrast" allows clean distinction for most signal points. Analysis of the data to determine effects of probe length shows no dramatic distinction between 21, 23 and 25 mer probes, although there is a cluster of 21 mer probes around 0 which indicates that the C and T probes are behaving similarly and not distinguishing well between methylated and unmethylated.

Mixtures of methylated and unmethylated DNA at varying percentages were tested including 0, 25, 50, 75 and 100% methylated. The points cluster in the expected order, with 100% being to the left of 75% which is to the left of 50% which is to the left of 25% which is to the left of 0%, but 75, 50 and 25 are shifted slightly to the left of expected, with 25% clustering around a sig contrast of 0, 50 at a sig contrast of about −0.25 and 75 at a sig contrast of about −0.75.

To determine how well the bisulfite read out works in the context of a more complex background (1) unmethylated genomic DNA (2) methylated genomic DNA or (3) unmethylated 2000-plex DNA generated from dU capture probes was treated with bisulfite, (1) and (2) were subjected to locus specific amplification, (3) was amplified using the common primers from the dU probes. The amplification products were either pooled prior to fragmentation and hybridization or fragmented and hybridized without pooling. The results indicate that even in a complex background of bisulfite converted unmethylated DNA the methylation states of the spike ins are clearly distinguishable.

Figure 3:
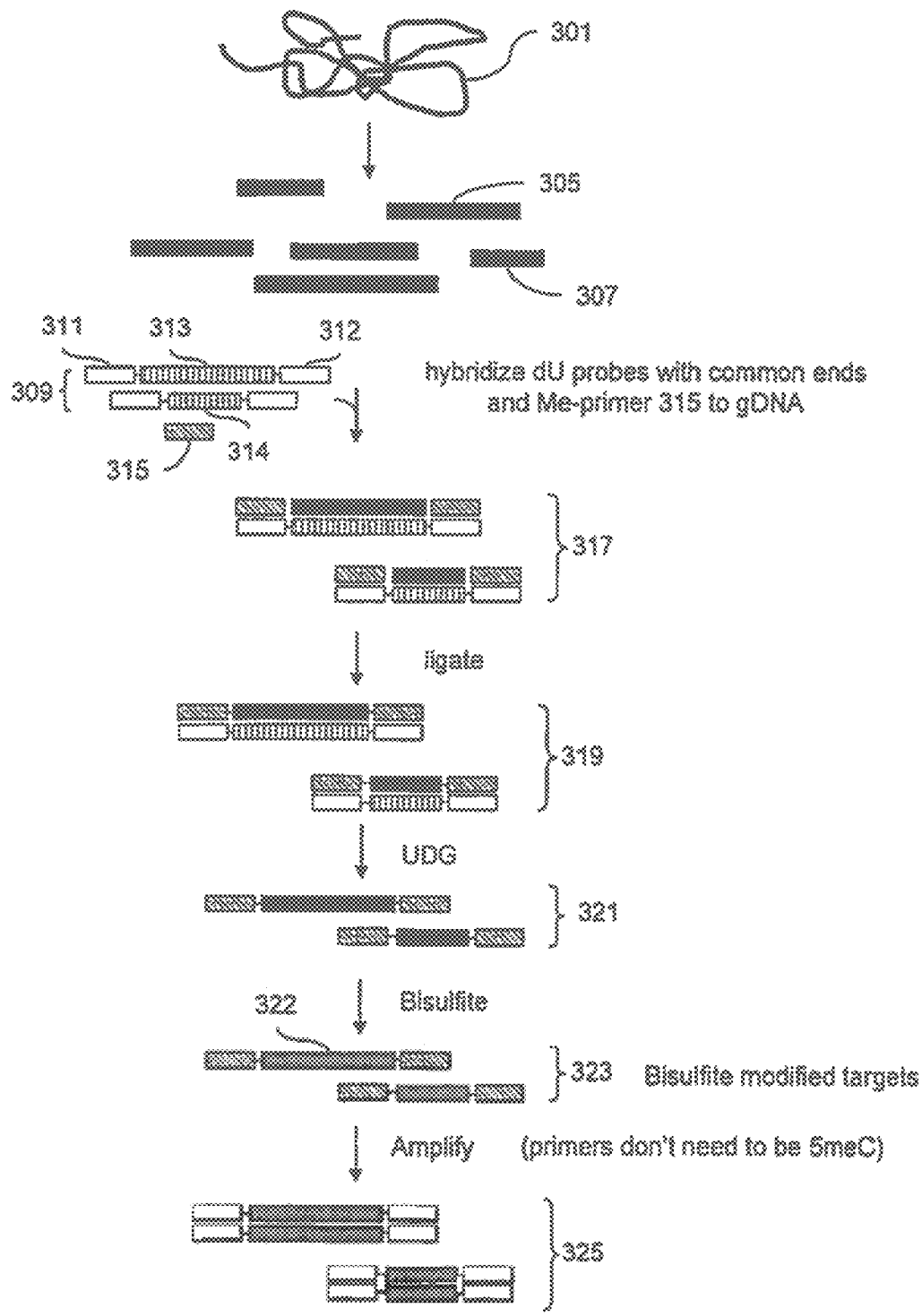
FIG. 3 is a schematic representation illustrating a method for using dU probes in conjunction with bisulfite modification to analyze methylation of a collection of pre-selected targets.

FIG. 3 illustrates an embodiment in which priming sites containing methylated cytosines are added to genomic DNA 301 using uracil containing target specific template probes 309. The uracil containing template probes each have a target specific region 313 and 314 that is flanked by common priming sites 311 and 312. The common priming sites may be the same or different. Oligonucleotide 315 is complementary to 311 and 312 and contains methylated cytosines that are resistant to bisulfite conversion. The oligonucleotide 315 and the genomic targets 305 and 307 hybridize to the dU probes to form duplexes 317. Ligation between the ends of targets 305 and 307 and oligonucleotides 315 results in product complexes [319] that include the targets with common primers ligated to either end in a complex with the complementary dU probe. The duplexes in 319 are subjected to UDG cleavage to digest 309 leaving singles started genomic DNA flanked by common priming sites [321]. The target sequences 305 and 307 hybridize to the target specific regions 313 and 314, respectively, of the template probes. The uracil containing probe is then digested with UDG to leave target genomic DNAs flanked by common priming sites [321] which are then treated with bisulfite to generate bisulfite modified genomic fragments 322 flanked by unmodified common priming sites [323] which are then amplified using primers to the common sequences to obtain multiplex amplified targets [325] that can be analyzed to determine if the cytosines from the genomic DNA were methylated or unmethylated. Analysis may be, for example, by hybridization to an array of probes with sequences that are specific for the sequence resulting from presence or absence of methylation, but other methods such as sequence specific PCR may also be used. See, for example, U.S. Pat. Nos. 6,265,171 and 6,200,756.

Figure 4:
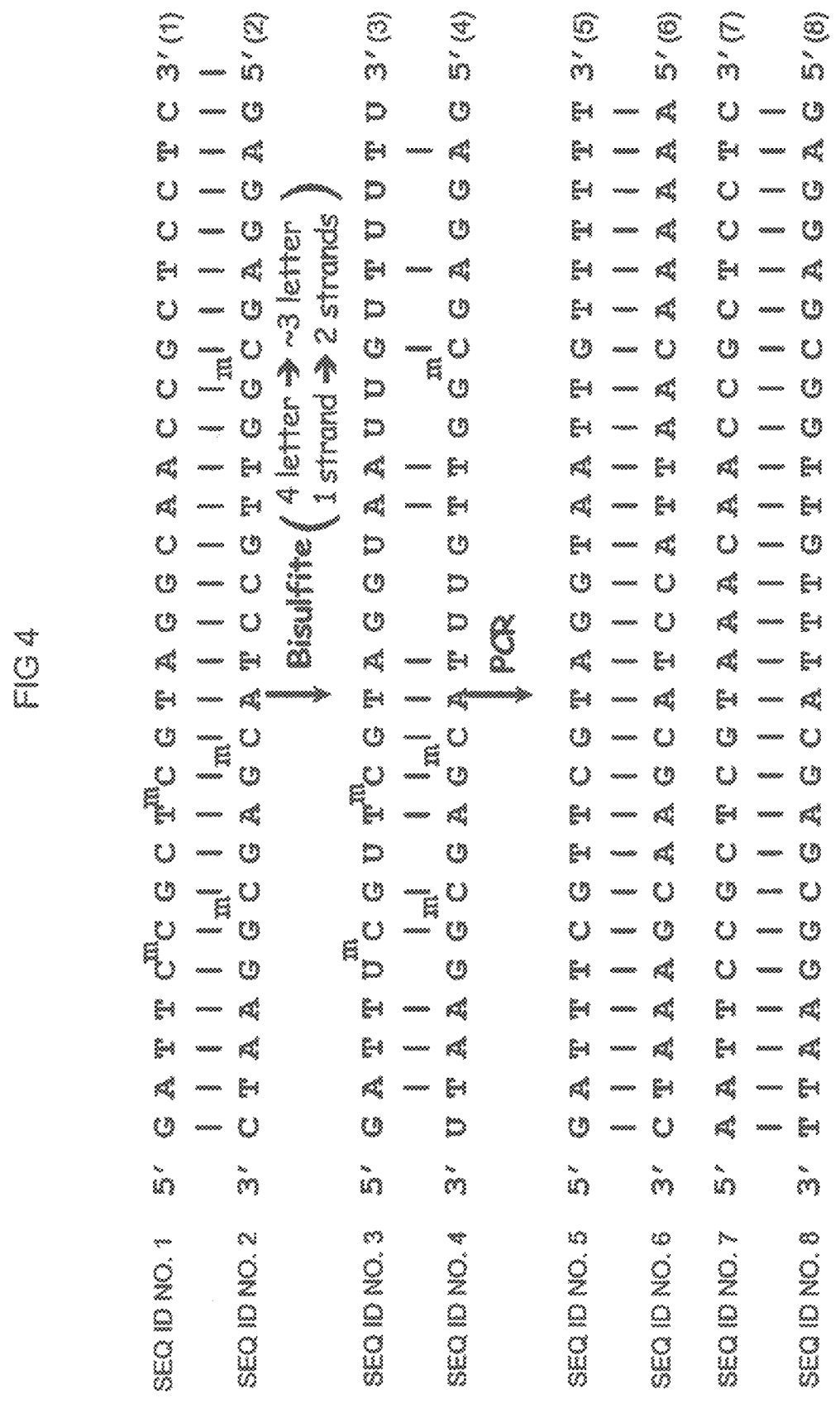

FIG. 4 illustrates the alteration of DNA sequence resulting from treatment of DNA with bisulfite. SEQ ID NOs. 1 and 2 are the complementary starting strands. Methylated cytosines are indicated by "m". SEQ ID NO. 3 corresponds to SEQ ID NO. 1 after treatment and SEQ ID NO. 4 corresponds to SEQ ID NO. 2 after treatment. Unmethylated cytosines have been converted to "U" and methylated cytosines remain "C". After PCR amplification SEQ ID NO. 3 gives SEQ ID NOs. 5 and 6, while SEQ ID NO. 4 results in SEQ ID NOs. 7 and 8. Many of the G-C base pairs from the starting sequence have been converted to A-T base pairs; resulting in a relatively low GC content for the final sequence.

FIG. 5 illustrates a method for methylation analysis of a selected group of target sequences using dU probe technology. Genomic DNA [501] is digested with one or more restriction enzymes to generate restriction fragments [503]. The restriction fragments are mixed with a collection of dU probes for specific targets [504] and common primer sequences [505] and the nucleic acids are denatured and allowed to anneal. The annealing step results in the formation of complexes between the dU probes, target fragments and primers [506]. There is a ligation step and a cleanup to enrich for the complexes with ligated targets, common primers and dU probes [507] and then the complexes are treated to digest the dU probes, leaving the targets ligated with primer sequences at either end [509]. These are treated with bisulfite to generate bisulfite modified targets flanked by common priming sequences [511] which may then be amplified by PCR to generate amplification products of the selected targets [513]. In this embodiment the primer sites are subjected to modification by bisulfite prior to amplification so steps should be taken to maintain the sequence of the primers. In one aspect the primers that are ligated to the target sequences contain 5-methyl cytosine so they are not changed in sequence by the bisulfite treatment. The amplification product is enriched for the targets of the dU probes. The amplification product is analyzed by hybridization to an array [515].

Figure 6A:
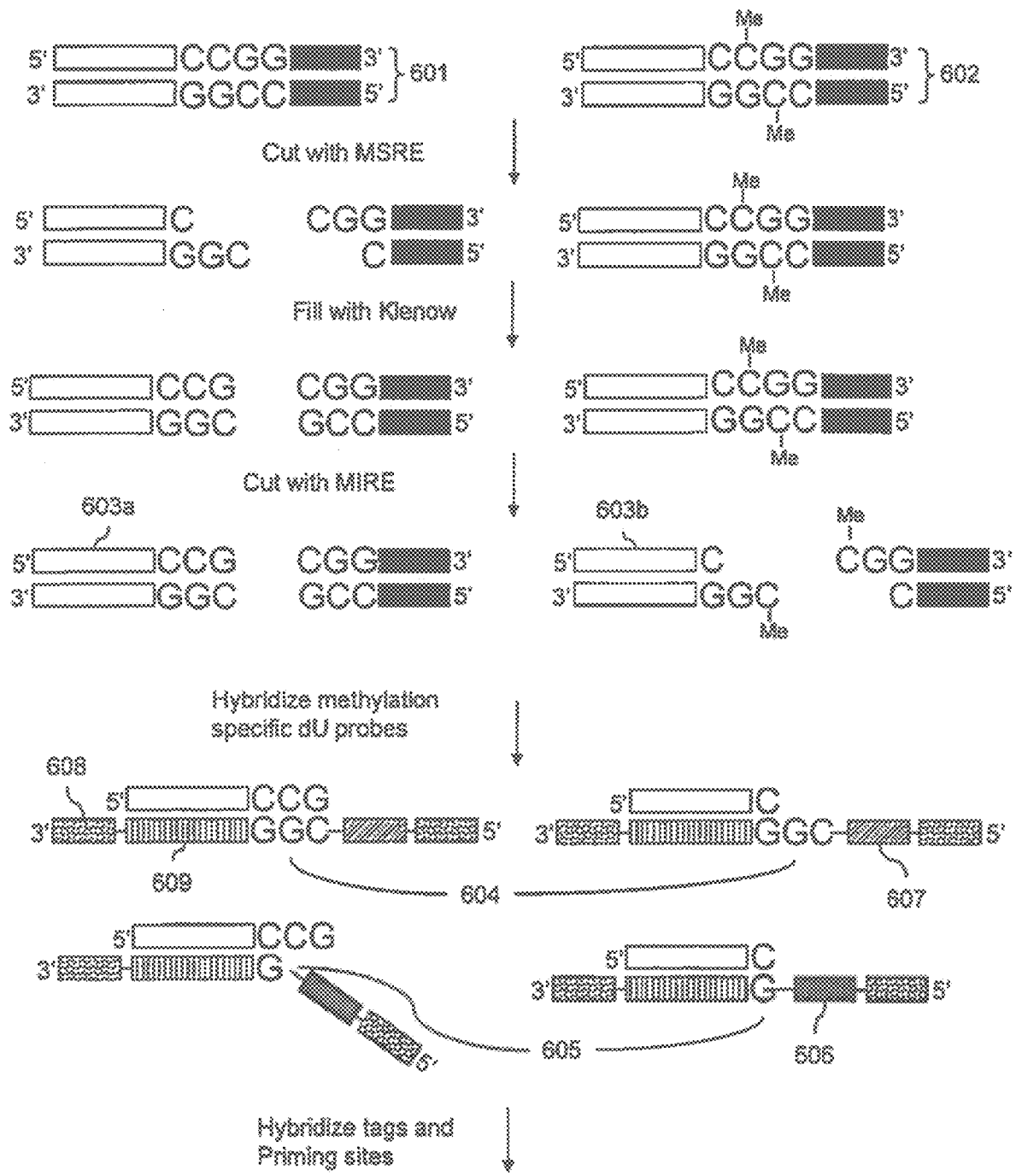

FIG. 6A illustrates a method of determining the methylation state of a cytosine in a methylation sensitive restriction site. Fragment 601 has an unmethylated MspI/HpaII site while fragment 602 has a methylated site. MspI and HpaII are isoschizomers with MspI being methylation insensitive and HpaII being methylation senstivei. The DNA is cleaved with HpaII so that unmethylated sites are cleaved while methylated sites remain uncleaved. The fragments are then end filled using Klenow. The DNA is then cleaved with the MspI so that the methylated sites are cleaved. The resulting fragments have one strand 603 that has a variable end sequence, the variation is the difference between end filling and no in filling. In the example illustrated the unmethylated fragment results in 603a with CCG at the 3' end and the methylated fragment results in 603b with C at the 3' end. The next step is the addition of dU probes that are specific for each type of fragment. Probe 604 is specific for 603a and probe 605 is specific for 603b. The dU probes have different tag sequences 606 and 607. The probes are shown hybridized to both fragments. The dU probes have common priming sequences 608 and target complementary region 609. The tags are optional and allow for differential detection. In FIG. 6B sequences that are complementary to the common priming sequences 608 and the tag sequences 606 and 607 are hybridized to the dU probes. Probes 604 and 605 can hybridize to either the product generated from the methylated or unmethylated sites but ligation between the 603a and 606 is blocked and ligation of 603b and 607 is blocked. Fragment 603a ligates with 607 and 608 to generate target 610 and fragment 603b ligates with 606 and 608 to generate target 611. The dU probes can then be digested to leave targets 610 and 611 which are tagged with either 606 or 607, depending on methylation, and are flanked by common priming sites 608. Targets 610 and 611 are amplified by PCR using a primer complementary to 608. The methylation state of the site can be determined by detecting which tag sequence or sequences are present in the amplified sample. If 607 is present the site was unmethylated and if 606 is present the site was methylated. The common priming sequences and the tag are ligated to the fragments in a methylation specific manner. The dU probe is digested and the products are amplified and the tags detected.

Figure 7A:
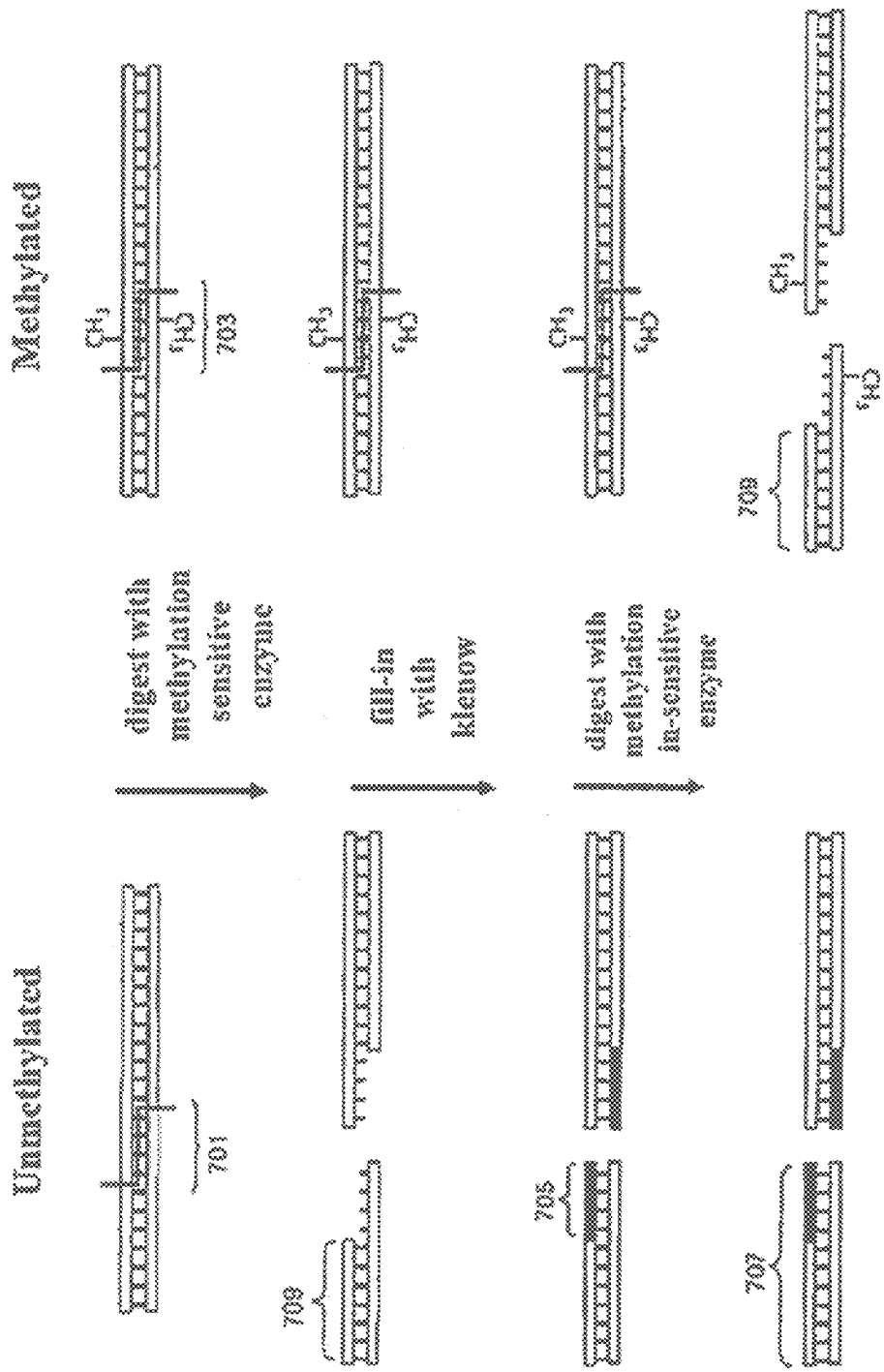

In FIG. 7A a fragment with an unmethylated restriction site [701] is shown on the left and a fragment where the site is methylated [703] is shown on the right. The fragments are digested with a methylation sensitive restriction enzyme so that the fragment on the left is cleaved but the fragment on the right is not. Klenow is added and the ends of the fragments on the left are end filled to add complementary sequences [705]. The products are then digested with a methylation insensitive enzyme so that the site in the fragment on the right is cleaved but the ends are not filled. The difference between strand 707 and strand 709 is that 707 has additional sequence 705—this is filled in and will be complementary to the fill-in specific probe while the sequence 709 is not filled in and will be targeted by the no-fill specific probe.

In FIG. 7B the different fragments 707 and 709 are differentially detected using dU probes. The dU probes include a probe [711] specific for 709 (no fill specific) and a probe [713] specific for 707 (fill-in specific). Probe 713 has an extra region [737] corresponding to the filled in region resulting from cleavage with the methylation sensitive enzyme. Probes 711 and 713 also vary in the sequence present at the tag complement regions, where 731c is complementary to tag 731 and 733c is complementary to tag 733. The dU probes can form complexes with the non-cognate targets to form complexes [715 and 717] but only the correctly formed complexes [719 and 721] provide the proper template for ligation of all the elements to form the complexes with the correctly ligated products [723 and 725]. After UDG treatment the ligated fragment products [727 and 729] are differentially labeled with different tags [731 and 733] and flanked by common primers [735] for amplification. The different tag sequences allow detection of the initial methylation event. If the site is methylated only 729 is detected (tag 731). If the site is unmethylated only 727 is detected (tag 733).

Figure 7C:
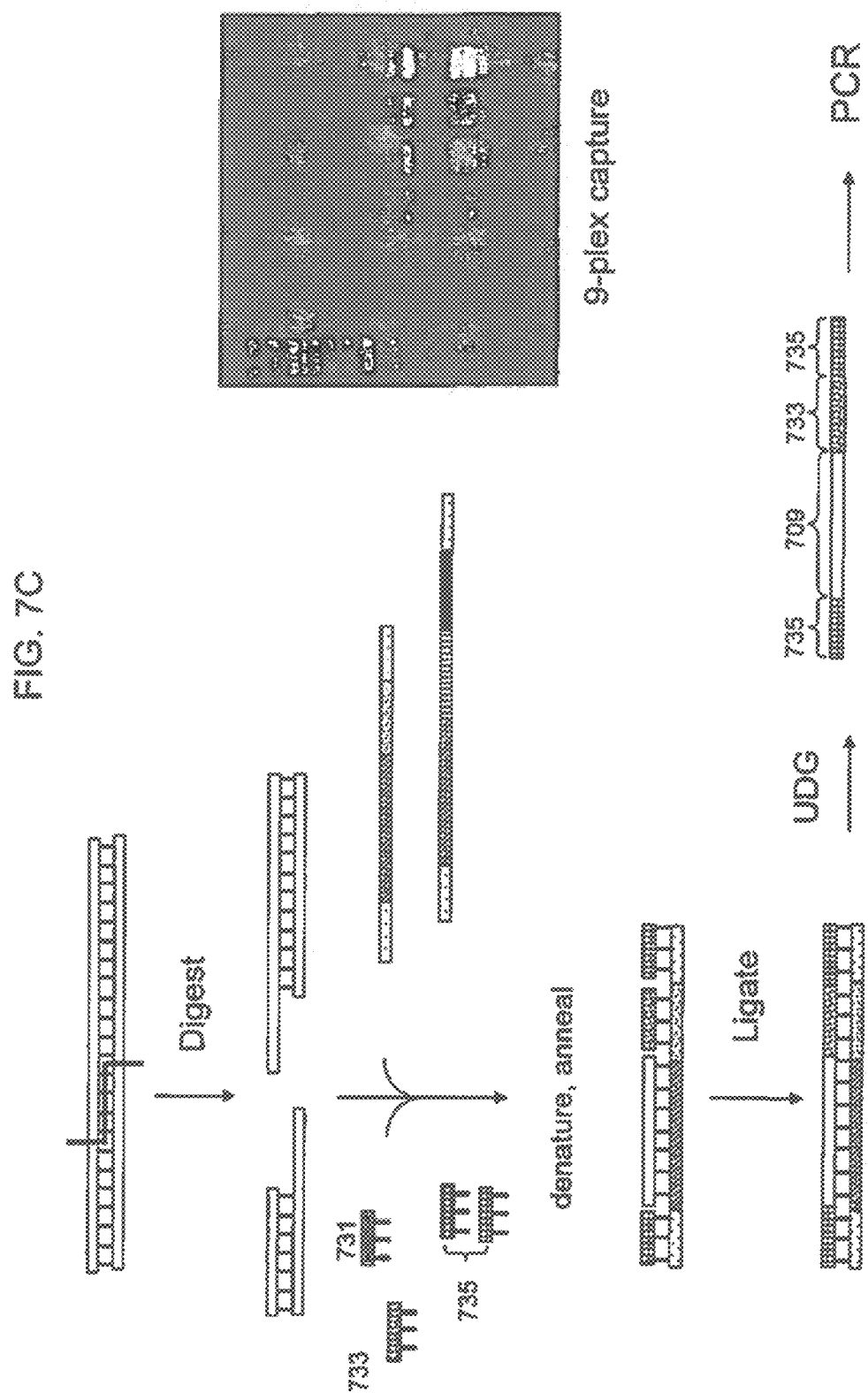

FIG. 7C shows a schematic of a dU probe capture experiment using dU probes for 9 different targets. The results are shown in the gel image on the right. The amount of dU probe added was varied in each reaction. Lane 1 is a standard ladder, lane 2 has no dU probe, lane 3 has 2 amol, lane 4 has 6, lane 5 has 18, lane 6 has 54, and lane 7 has 162. Two different dU probes are shown schematically. There is 0.1 amol of the target present.

Figure 8:
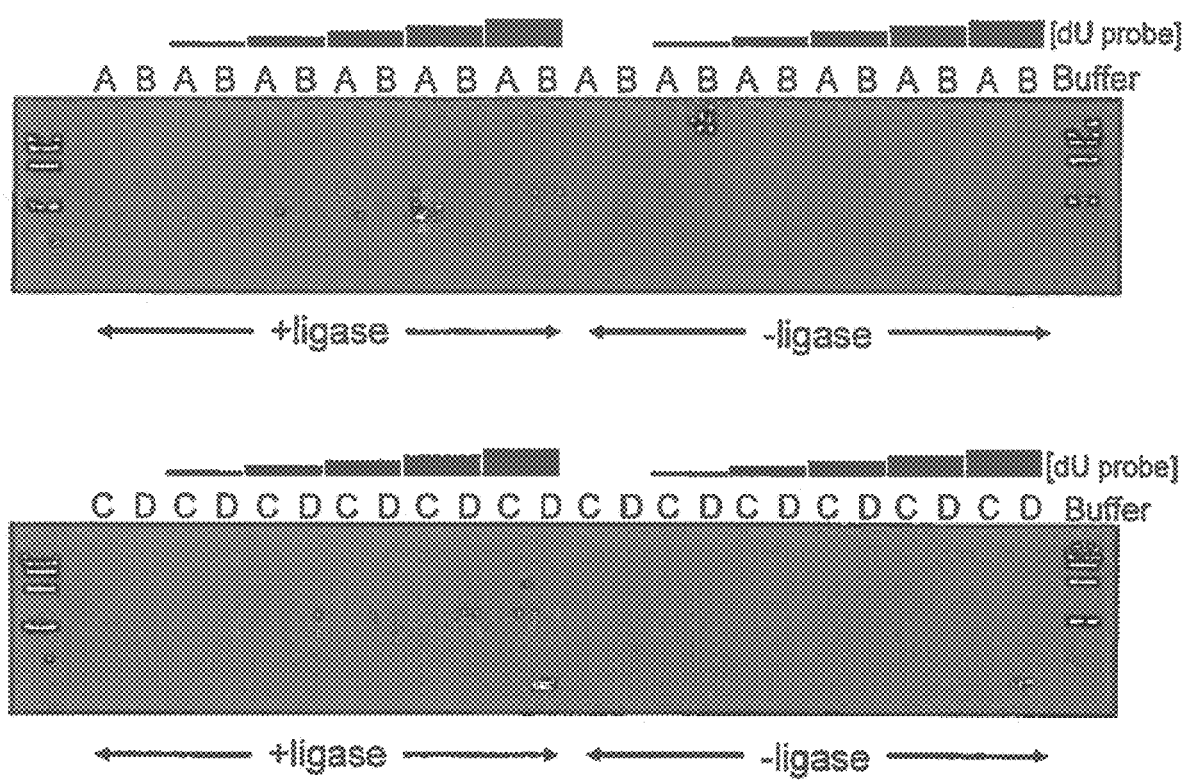
FIG. 8 shows 384 multiplex amplification using dU probes.

FIG. 8 shows the results of 384-plex capture using a mixture of 384 target specific dU probe methodology. Stained agarose gel images are shown. The reactions run on the upper gel used either Buffer A (15 mM $MgCl_2$, 33 mM Tris-HCl pH 7.5, 0.1 mg/ml BSA) or Buffer B (33 mM Tris-acetate pH 7.9, 10 mM $MgCl_2$, 66 mM K-acetate, 0.1 mg/ml BSA) as indicated and the reactions run on the lower gel used either Buffer C (33 mM Tris-acetate pH 7.9, 10 mM MgCl$_2$, 66 mM K-acetate, 0.1 mg/ml BSA, 0.2 U Primer Navigator) or Buffer D (6×SSPE, 7.5% PEG-8000) as indicated. The reactions on the left have ligase while the reactions on the right are without ligase. As expected, amplification products are only observed in the presence of ligase. Each of the different buffer conditions gave specific amplification products in the expected size range. Buffer A gives more amplification product than Buffer B at lower dU probe concentrations. The reactions have increasing amounts of dU probe as indicated graphically above each gel image.

In many embodiments one or more reaction conditions may be varied. In some aspects the basic starting conditions are 6×SSPE with 7.5% PEG, the annealing conditions are 94° C. for 1 min, 70° C. for 40 min, 65° C. for 40 min, 60° C. for 40 min, 55° C. for 10 min, and 50° C. for 10 min. Other ranges of conditions that may be used include 0-15 mM MgCl$_2$, 0-200 mM KCl, variation of the pH, addition of RecA and SSB, including the use of thermophilic SSB, and variation of the reaction volume.

Figure 9:
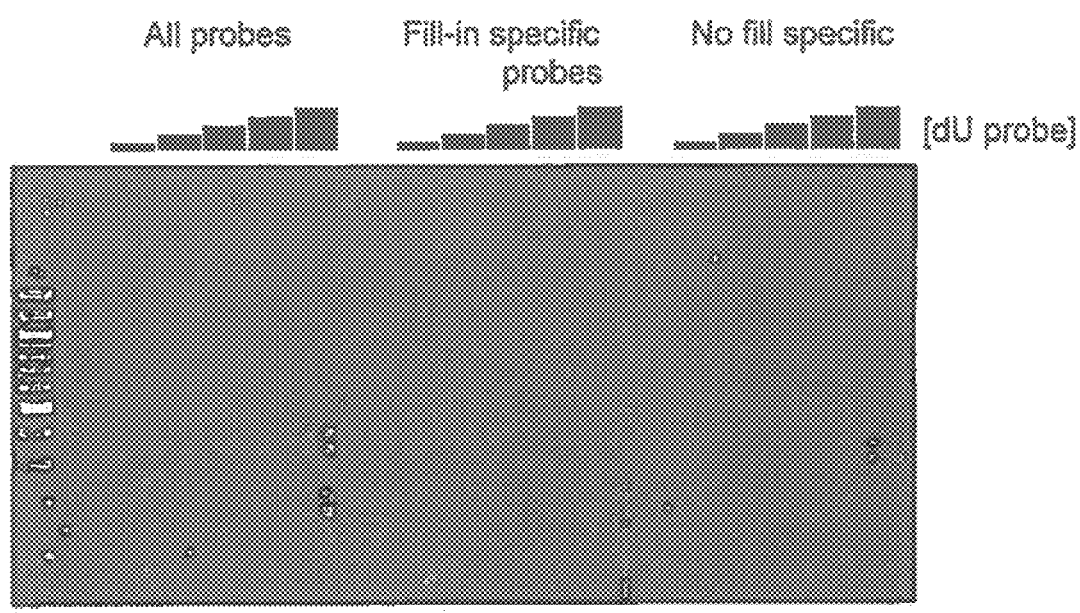
FIG. 9 shows a gel image of dU capture following cleavage using fill-in and no fill specific probes as illustrated schematically in FIG. 7

FIG. 9 shows an image of a gel separating the products of amplification in the presence of fill-in specific probes (center) or no fill specific probes (right side of gel) or both (left side of gel). HpaII and MspI are the enzymes used. The genomic DNA is from liver.

In preferred aspects there are 200-1000, 1000-2500, 2000-5000, 5000-10,000, 10,000-20,000 or more than 20,000 different target sequences analyzed. There may be a dU probe for each target sequence to be amplified.

In another aspect, common priming sites are added to each of a plurality of templates of distinct sequence by first hybridizing locus specific primers to the targets and extending the locus specific primers.

Many methods of determining the genotype or methylation status of two positions that are near to one another do not provide information about chromosome. For example, if SNP1 and SNP2 are in the same gene and both are interrogated and found to be heterozygotes (A/B) there are 4 possibilities for the each copy of the gene—it could be A for SNP1 and A for SNP2, B for SNP1 and B for SNP2, A for SNP1 and B for SNP2 or B for SNP1 and A for SNP2. The genotypes of the individual SNPs don't provide information about the genotype of the neighboring SNPs unless there is additional information about linkage. Similarly, if the methylation state of a cytosine is determined by bisulfite modification based analysis it may be useful to determine if both C's are methylated on the same chromosome or on different chromosomes.

Figure 10:
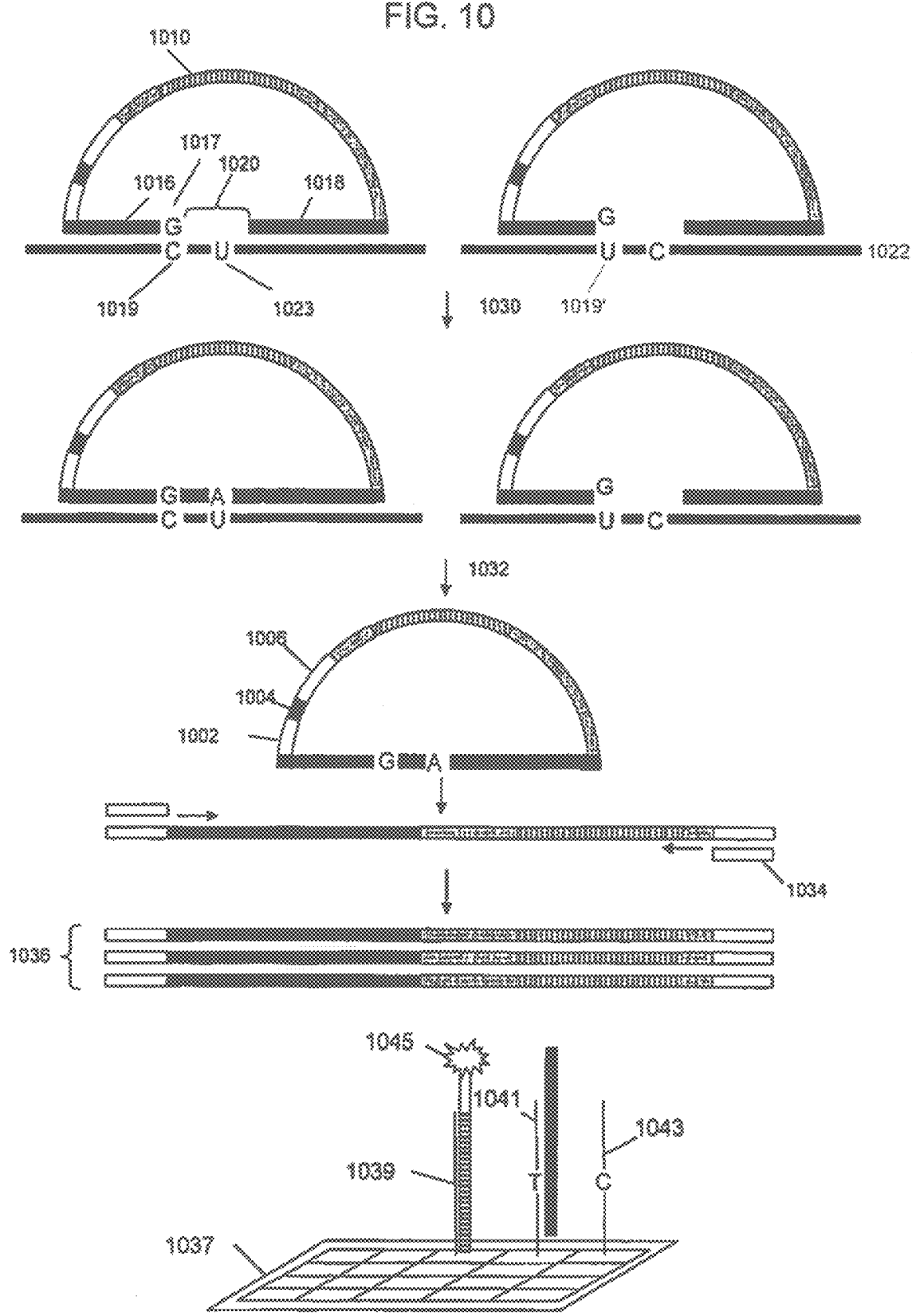
FIG. 10 is a schematic representation illustrating embodiments for determining the epihaplotype of two neighboring cytosines.

Analysis of determining "epihaplotypes" using inversion probes are shown in FIG. 10. In one embodiment molecular inversion probe methods are used to analyze the methylation status of neighboring cytosines. When determining the genotype of two neighboring or linked SNPs in a diploid organism, many methods do not provide information about what the haplotype is, for example, if SNP1 is heterozygous A/G and SNP2 is heterozygous C/T, there is no information about how the SNPs are combined on each of the chromosomes. It would be useful to know if the A allele of SNP 1 is linked to the C or T allele of SNP 2 or if the G allele of SNP 1 is linked to the C or T allele of SNP 2 Similarly, with methylation in a diploid it may be desirable to know if two neighboring cytosines are both methylated in one copy of the gene and not methylated in the other copy. In one aspect genomic DNA is treated with bisulfite to differentially modify methylated and unmethylated cytosines. Each MIP has an interrogation position corresponding to a first cytosine position (1019) and the second cytosine position (1020) is positioned between the target complementary arms (1016 and 1018) of the MIP. In the figure, the interrogation base (1017) of the MIP is shown as a G corresponding to methylation at 1019. One of skill in the art will recognize that a MIP probe could be designed with a T at the interrogation position which would circularize only if the position was unmethylated. Similarly, the MIP probe could be designed so that the interrogation position was complementary to position 1023 with or without methylation and position 1019 could be positioned in the gap between 1016 and 1018. A label (1045) may be used to detect a hybridized tag sequence.

As shown in the figure, the G at 1017 hybridizes to the C at 1019 and can be extended to fill the gap 1020, including the complement of position 1023. In the chromosome (1022) where position 1019' was not methylated and was converted to a U by bisulfate, the G does not hybridize efficiently and is not extended to fill in the gap. After gap filling and ligation step (1030) the MIP on the left is circular while the MIP on the right is linear. Linear MIPs may be digested by exonuclease in step 1032 and the remaining circular probes can be linearized at the cleavage site 1004 and amplified using primers 1034 complementary to the primer sites 1002 and 1006. The amplified fragments 1036 can be interrogated for both the presence of tag sequences 1010 and for the sequence present at the second cytosine position. The presence of the tag indicates the methylation status of position 1019, if tag 1010 is present position 1019 was methylated. The methylation status of position 1023 is interrogated by allele specific hybridization. MIP probes for different methylation states of position 1019 have different tags and are separated into separate reactions. The array (1037) has probe 1039 to tag 1010 and probe 1041 and 1043 that are complementary to portions of 1016 and 1018 and to gap 1020 with 1041 being perfectly complementary to the gap generated if position 1023 was not methylated and probe 1043 being perfectly complementary to the gap generated if position 1023 was methylated. This method may also be used to detect the genotypes of two neighboring SNPs.

Figure 11:
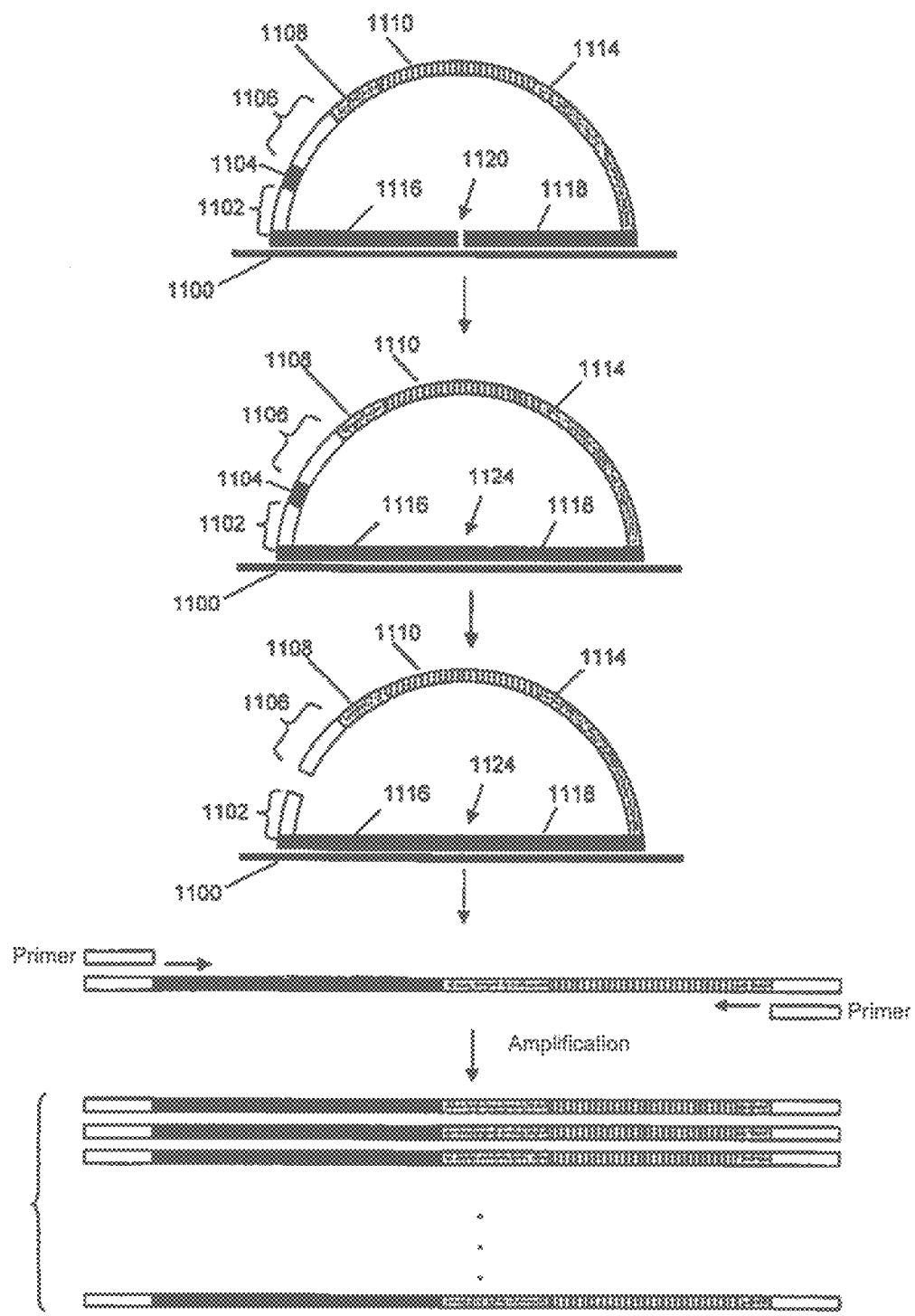
FIG. 11 is a schematic representation illustrating the use of molecular inversion probes.

FIG. 11 shows a schematic of a method of forming a closed circular probe from a linear MIP. For additional details on features of molecular inversion probes and methods of using molecular inversion probes see U.S. Pat. No. 6,858,412 which is incorporated herein in its entirety for disclosure of methods related to MIP. The MIP has sequences 1116 and 1118 that are complementary to template 1100 and hybridize to 1100 leaving a gap 1120. The gap may be 1 or more bases or it may be simply a break in the phosphate backbone that may be closed by ligation. The MIP also has barcode sequence 1110, priming sites 1102 and 1106, first cleavage site 1104 and optional spacer sequences 1108 and 1114 which can contain other functional sequences such as priming sites, restriction sites, promoter sites, additional barcode sequences or detectable labels.

An optional extension of either 1116 or 1118 (depending on which has a free 3' end) may be used to fill in the gap at 1120 followed by ligation of the free ends of the linear probe at 1124. Linear probes may be digested by exonuclease treatment. Circular probes may then be linearized, for example by cleavage at 1104. In one aspect the cleavage site 1104 comprises one or more uracil bases. The probe may be treated after the ligation step with uracil-DNA glycosylase ("UDG"), which catalyzes the release of free uracil from uracil-containing DNA, creating apurinic ("AP") sites. AP sites may then be cleaved enzymatically using an AP endonuclease or, under certain conditions, an AP lyase. For example, the AP site may be cleaved using Apel, an Endo IV or Fpg (formamidopyrimidine [fapy]-DNA glycosylase; also known as 8-oxoguanine DNA glycosylase). Fpg cleaves both 3' and 5' to the AP site, removing the AP site and leaving a 1 base gap. Alternatively, the AP sites may be cleaved chemically, such as by treatment with 1,4 diaminobutane and heat. AP sites may also be cleaved by exposure to high pH.

Figure 12:
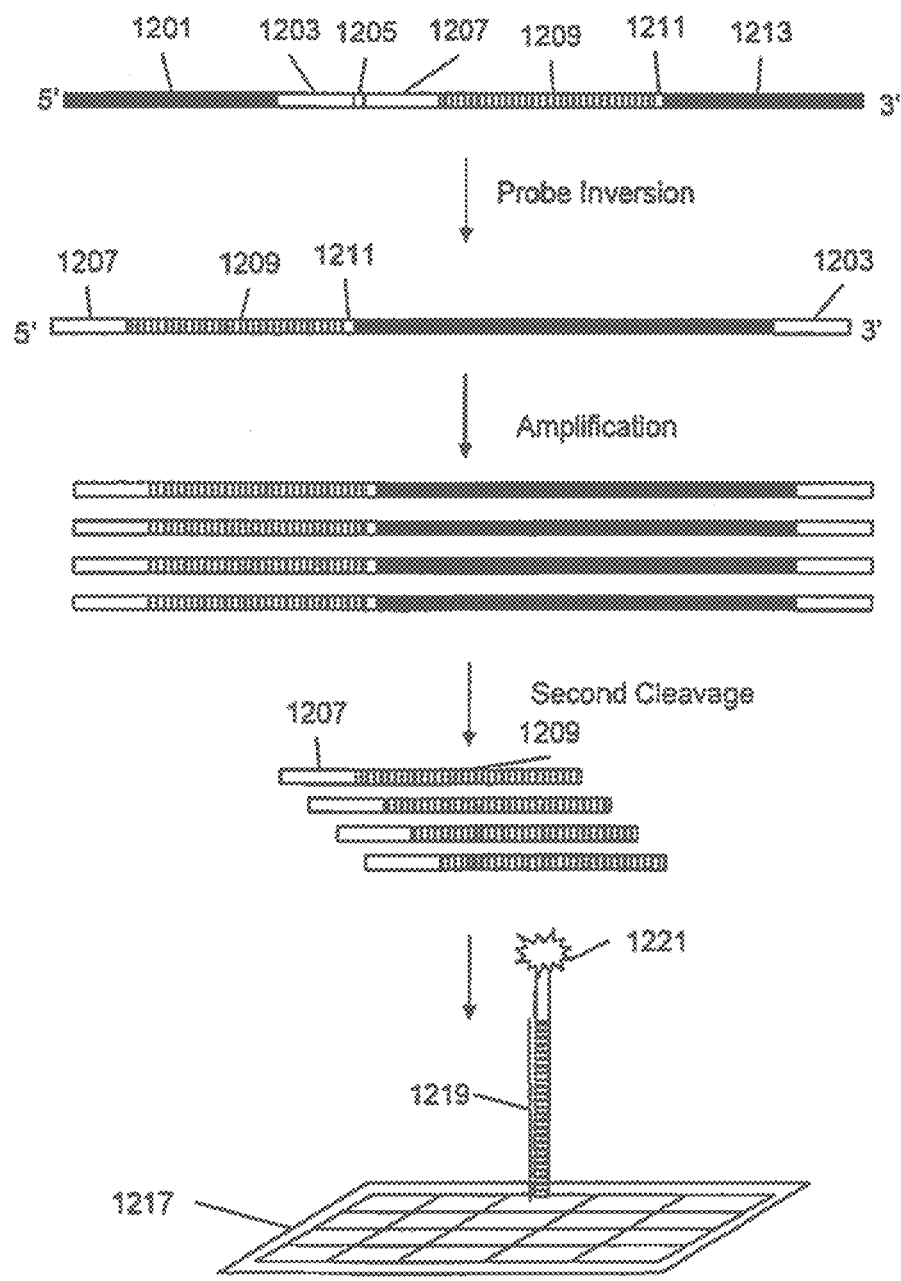
FIG. 12 is a schematic illustrating probe inversion, amplification, and detection of a tagged fragment.

FIG. 12 shows a MIP before and after probe inversion. Before inversion the ends are 1201 and 1213. After circularization and cleavage at 1205 (probe inversion) the ends are 1207 and 1203. Primers for 1207 and 1203 are used to amplify the inverted probe. The amplification products are typically double stranded while the probe is single stranded. The amplification products can be cleaved at 1211 to separate 1207 and 1209 from the remainder of the probe. The tag sequence [1209] may be detected by hybridization to an array [1217] of tag probes [1219]. A label [1221] may be used to detect a hybridized tag sequence.

In some aspects the probes can include purines at a cleavage site such as 8-oxoguanine, 8-oxoadenine, fapy-guanine, methyl-fapy-guanine, fapy-adenine, aflatoxin B-fapy-guanine, 5-hydroxy-cytosine, and 5-hydroxy-uracil, that mimic damaged purines. Fpg glycosylase will release these residues from DNA and remove the resulting AP site, leaving a 1 nucleotide gap.

The probe may be amplified after circularization. Circularized probes that have been linearized may be amplified, for example by PCR using primers to regions 502 and 506. Other methods of amplification may also be used. For example, rolling circle amplification may be used to generate multiple copies of the circularized probes. See, for example, U.S. Pat. Nos. 5,648,245 and 5,854,033 and Fire and Xu, Proc NatlAcad Sci USA 92:4641-5 (1995). As used herein, the term amplification includes the production of RNA transcripts by polymerization driven from a phage promoter. For example, a T7 RNA polymerase promoter sequence may be incorporated into the probe and used to generate multiple RNA copies using a T7 RNA polymerase.

In preferred aspects, the amplification product is DNA produced by polymerization primed using one or more oligonucleotides ("primers") that are capable of hybridizing to one or more priming sites within one or more of the oligonucleotides appended to the template. For example, a first primer capable of binding to a first priming site present in the first oligonucleotide may be used to prime unidirectional amplification. A second primer capable of binding to the complement of the second priming site present in the second oligonucleotide may be used concurrently to prime bidirectional amplification. In embodiments in which first and second priming sites are reverse complements of one another, the first and second primers may be the same. Amplification may be isothermal or thermal cycling.

Nucleic acid amplification methods useful in the methods of the present invention are well known in the art and include, e.g., polymerase chain reaction (PCR), nucleic acid sequence-based amplification (NASBA), self-sustained sequence recognition (3SR), ligase chain reaction (LCR), transcription-mediated amplification (TMA), rolling circle amplification (RCA), and strand displacement amplification (SDA).

In another aspect the enzyme CIRCLIGASE (Epicenter) which ligates single stranded DNAs into circles may be used. DNA fragments may be denatured after digestion and CIRCLIGASE may be used to circularize the fragments after bisulfite treatment. The circles may then be amplified, for example by rolling circle amplification. The enzyme is thermostable and ATP-dependent, but will ligate ends of ssDNA in the absence of a complementary sequence without the requirement that the ends be annealed adjacently on one another.

In another aspect one or more of the methods disclosed herein is combined with the use of affinity bases pull-downs of 5mC containing DNA. Antibodies that recognize 5mC are commercially available. For example, ABCAM sells a 5-methyl cytosine antibody (ab1884).

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention may be practiced by other than the described embodiments, which are presented for purposes of illustration only and not by way of limitation. The present invention is limited only by the claims that follow.

What is claimed is:

1. A method for analyzing the methylation of a plurality of cytosines in a plurality of target sequences, said method comprising:
   (a) obtaining a genomic DNA sample;
   (b) fragmenting the genomic DNA sample with a methylation-sensitive restriction enzyme (MSRE) to obtain fragments, wherein said fragments comprise a mixture of target fragments and non-target fragments;
   (c) filling in the ends generated by cleavage with the MSRE using a DNA polymerase;
   (d) fragmenting the product of (c) with a methylation-insensitive restriction enzyme (MIRE) that recognizes the same restriction site as the MSRE;
   (e) mixing the fragments of (d) with (i) a plurality of template probes, each template probe comprising a target complementarity region, a first common priming sequence and a second common priming sequence, wherein said first common priming sequence is 3' of the target complementarity region and said second common priming sequences is 5' of the target complementarity region, (ii) an oligonucleotide complementary to said first common priming sequence and an oligonucleotide that is complementary to said second common priming sequence, wherein at least one of the oligonucleotides is exonuclease-resistant, and (iii) a ligase, to obtain ligation products;

(f) treating the products of (e) with an exonuclease to digest the template probes;
(g) treating the products of (f) with bisulfite;
(h) amplifying the products of (g) by PCR using primers to the common priming sequences to obtain an amplification product;
(i) hybridizing the amplification product from step (h) to an array of probes to obtain a hybridization pattern; and
(j) analyzing the hybridization pattern to detect the presence or absence of methylation at a plurality of cytosines in the target sequences.

2. The method of claim 1 wherein the exonuclease is a 5' to 3' exonuclease and the oligonucleotide complementary to said first common priming sequence is resistant to 5' to 3' exonuclease digestion.

3. The method of claim 1 wherein the oligonucleotide complementary to said first common priming sequence comprises a plurality of phosphorothioate linkages.

4. The method of claim 1 wherein the exonuclease is a 3' to 5' exonuclease and the oligonucleotide complementary to said second common priming sequence is resistant to 3' to 5' exonuclease digestion.

5. The method of claim 1 wherein the array comprises a first plurality of probes that are perfectly complementary to a genomic region containing a CpG after bisulfite treatment and amplification if the region was unmethylated and a second plurality of probes that are perfectly complementary to the same region after bisulfite modification and amplification if the region was fully methylated.

6. The method of claim 1 wherein the common priming sequences contain 5-methylcytosine in place of cytosine.

* * * * *

SEQUENCE LISTING

<160> NUMBER OF SEQ ID NOS: 19

<210> SEQ ID NO 1
<211> LENGTH: 27
<212> TYPE: DNA
<213> ORGANISM: Artificial
<220> FEATURE:
<223> OTHER INFORMATION: Synthetic

<400> SEQUENCE: 1
gattccgctc gtaggcaacc gctcctc                                         27

<210> SEQ ID NO 2
<211> LENGTH: 27
<212> TYPE: DNA
<213> ORGANISM: Artificial
<220> FEATURE:
<223> OTHER INFORMATION: Synthetic

<400> SEQUENCE: 2
gaggagcggt tgcctacgag cggaatc                                               27

<210> SEQ ID NO 3
<211> LENGTH: 27
<212> TYPE: DNA
<213> ORGANISM: Artificial
<220> FEATURE:
<223> OTHER INFORMATION: Synthetic

<400> SEQUENCE: 3
gattucgutc gtagguaauu gutuutu                                               27

<210> SEQ ID NO 4
<211> LENGTH: 27
<212> TYPE: DNA
<213> ORGANISM: Artificial
<220> FEATURE:
<223> OTHER INFORMATION: Synthetic

<400> SEQUENCE: 4
gaggagcggt tguutacgag cggaatu                                               27

<210> SEQ ID NO 5
<211> LENGTH: 27
<212> TYPE: DNA
<213> ORGANISM: Artificial
<220> FEATURE:
<223> OTHER INFORMATION: Synthetic

<400> SEQUENCE: 5
gatttcgttc gtaggtaatt gtttttt                                               27

<210> SEQ ID NO 6
<211> LENGTH: 27
<212> TYPE: DNA
<213> ORGANISM: Artificial
<220> FEATURE:
<223> OTHER INFORMATION: Synthetic

<400> SEQUENCE: 6
aaaaaacaat tacctacgaa cgaaatc                                               27

<210> SEQ ID NO 7
<211> LENGTH: 27
<212> TYPE: DNA
<213> ORGANISM: Artificial
<220> FEATURE:
<223> OTHER INFORMATION: Synthetic

<400> SEQUENCE: 7
aattccgctc gtaaacaacc gctcctc                                               27

<210> SEQ ID NO 8
<211> LENGTH: 27
<212> TYPE: DNA
<213> ORGANISM: Artificial
<220> FEATURE:
<223> OTHER INFORMATION: Synthetic

<400> SEQUENCE: 8
gaggagcggt tgtttacgag cggaatt                                               27

<210> SEQ ID NO 9
<211> LENGTH: 13
<212> TYPE: DNA
<213> ORGANISM: Artificial

```
<220> FEATURE:
<223> OTHER INFORMATION: Synthetic

<400> SEQUENCE: 9
gacgaacgcg gct                                                        13

<210> SEQ ID NO 10
<211> LENGTH: 13
<212> TYPE: DNA
<213> ORGANISM: Artificial
<220> FEATURE:
<223> OTHER INFORMATION: Synthetic

<400> SEQUENCE: 10
gacgaacgtg gct                                                        13

<210> SEQ ID NO 11
<211> LENGTH: 13
<212> TYPE: DNA
<213> ORGANISM: Artificial
<220> FEATURE:
<223> OTHER INFORMATION: Synthetic

<400> SEQUENCE: 11
gacgaatgtg gct                                                        13

<210> SEQ ID NO 12
<211> LENGTH: 13
<212> TYPE: DNA
<213> ORGANISM: Artificial
<220> FEATURE:
<223> OTHER INFORMATION: Synthetic

<400> SEQUENCE: 12
gatgaatgtg gct                                                        13

<210> SEQ ID NO 13
<211> LENGTH: 13
<212> TYPE: DNA
<213> ORGANISM: Artificial
<220> FEATURE:
<223> OTHER INFORMATION: Synthetic

<400> SEQUENCE: 13
gatgaatgcg gct                                                        13

<210> SEQ ID NO 14
<211> LENGTH: 13
<212> TYPE: DNA
<213> ORGANISM: Artificial
<220> FEATURE:
<223> OTHER INFORMATION: Synthetic

<400> SEQUENCE: 14
gatgaacgcg gct                                                        13

<210> SEQ ID NO 15
<211> LENGTH: 13
<212> TYPE: DNA
<213> ORGANISM: Artificial
<220> FEATURE:
<223> OTHER INFORMATION: Synthetic

<400> SEQUENCE: 15
gacgaatgcg gct                                                        13
```

```
<210> SEQ ID NO 16
<211> LENGTH: 13
<212> TYPE: DNA
<213> ORGANISM: Artificial
<220> FEATURE:
<223> OTHER INFORMATION: Synthetic

<400> SEQUENCE: 16
gatgaacgtg gct                                                              13

<210> SEQ ID NO 17
<211> LENGTH: 189
<212> TYPE: DNA
<213> ORGANISM: Artificial
<220> FEATURE:
<223> OTHER INFORMATION: Synthetic

<400> SEQUENCE: 17
agctggtgat gctgatcaga gcctctgtag tcttaaatga cttttctaac taattctaaa           60
tcttcagaac ccatcgtata aaaaggccat accttctgga gggacgtcga tggtattagg          120
atagaagcac caggggaccc cacgaacggt gtcgtcgaaa cagcagccct tatttgcaca          180
ctgggaggg                                                                  189

<210> SEQ ID NO 18
<211> LENGTH: 127
<212> TYPE: DNA
<213> ORGANISM: Artificial
<220> FEATURE:
<223> OTHER INFORMATION: Synthetic

<400> SEQUENCE: 18
gggaccaccc ttataaggct cggaggccgc gaggccttcg ctggagtttc gccgccgcag           60
tcttcgccac cagtgagtac gcgcggcccg cgtccccggg gatgggctc agagctccca          120 gcatggg                                                                    127

<210> SEQ ID NO 19
<211> LENGTH: 144
<212> TYPE: DNA
<213> ORGANISM: Artificial
<220> FEATURE:
<223> OTHER INFORMATION: Synthetic

<400> SEQUENCE: 19
gcaggggagg gaagcagatg ccagcgggcc gaagagtcgg gagccggagc cgggagagcg           60
aaaggagagg ggacctggcg gggcacttag gagccaaccg aggagcagga gcacggactc         120
ccactgtgga aaggaggacc agaa                                                 144
```